(12) United States Patent
Topper et al.

(10) Patent No.: US 10,973,511 B2
(45) Date of Patent: Apr. 13, 2021

(54) SUTURING APPARATUS AND METHOD

(71) Applicant: MEDOS INTERNATIONAL SARL, Le Locle (CH)

(72) Inventors: Brad Topper, Santa Clarita, CA (US); Thomas Weisel, Ventura, CA (US); J. Terry Benson, West Hills, CA (US); Brett Bannerman, Canyon Country, CA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 123 days.

(21) Appl. No.: 16/035,400

(22) Filed: Jul. 13, 2018

(65) Prior Publication Data

US 2018/0325511 A1     Nov. 15, 2018

Related U.S. Application Data

(60) Division of application No. 14/207,188, filed on Mar. 12, 2014, now Pat. No. 10,034,665, which is a
(Continued)

(51) Int. Cl.
    *A61B 17/06*          (2006.01)
    *A61B 17/04*          (2006.01)
    (Continued)

(52) U.S. Cl.
    CPC .... *A61B 17/06066* (2013.01); *A61B 17/0469* (2013.01); *A61B 17/0483* (2013.01);
(Continued)

(58) Field of Classification Search
    CPC .......... A61B 17/06066; A61B 17/0469; A61B 17/0483; A61B 17/0625; A61B 2017/06095
    See application file for complete search history.

(56) References Cited

U.S. PATENT DOCUMENTS

| 17,272 A | 5/1857 | Garvey |
| 527,263 A | 10/1894 | Blanchard |

(Continued)

FOREIGN PATENT DOCUMENTS

| CN | 2862986 Y | 12/2005 |
| DE | G9214276.1 | 10/1922 |

(Continued)

OTHER PUBLICATIONS

Partial European Search Report dated Oct. 13, 2017, for related European case No. 17151871.5.
(Continued)

*Primary Examiner* — Tuan V Nguyen
(74) *Attorney, Agent, or Firm* — Myers Andras LLP; Joseph C. Andras

(57) ABSTRACT

A suturing apparatus comprises a pair of jaws. A bendable needle housed in one of the jaws is adapted to carry a suture. A suture receiver is disposed adjacent to, or integral with, the opposite jaw to help disengage the suture carried by the bendable needle. A transition block curves the needle and directs it in a direction generally unparallel to an axis of the carrying jaw. The jaw housing the needle may include a lateral opening through which the suture may be inserted. The needle may also include a lateral notch which may be aligned with lateral opening to receive the suture. An actuator coupled to the needle enables the user to move the needle proximally to align the notch with the lateral slot.

6 Claims, 37 Drawing Sheets

Related U.S. Application Data continuation of application No. 13/855,900, filed on Apr. 3, 2013, now Pat. No. 9,808,241, which is a division of application No. 12/971,457, filed on Dec. 17, 2010, now Pat. No. 8,540,732, which is a division of application No. 11/738,129, filed on Apr. 20, 2007, now Pat. No. 7,879,046, which is a continuation-in-part of application No. 10/255,523, filed on Sep. 25, 2002, now Pat. No. 7,377,926.

(60) Provisional application No. 60/326,287, filed on Oct. 1, 2001, provisional application No. 60/358,960, filed on Feb. 25, 2002.

(51) Int. Cl.
   *A61B 17/062* (2006.01)
   *A61B 90/00* (2016.01)
   *A61B 17/28* (2006.01)

(52) U.S. Cl.
   CPC ...... *A61B 17/0625* (2013.01); *A61B 2017/06042* (2013.01); *A61B 2017/06095* (2013.01); *A61B 2017/2837* (2013.01); *A61B 2017/2845* (2013.01); *A61B 2090/0814* (2016.02)

(56) References Cited

U.S. PATENT DOCUMENTS

| | | |
|---|---|---|
| 1,037,864 A | 9/1912 | Saxton |
| 1,449,087 A | 3/1923 | Bugbee |
| 1,464,832 A | 8/1923 | Richardson |
| 1,500,884 A | 7/1924 | Jones |
| 1,641,077 A | 8/1927 | Fouquet |
| 1,822,330 A | 9/1931 | Ainslie |
| 2,303,956 A | 12/1942 | Vollrath |
| 2,738,790 A | 3/1956 | Todt, Sr. et al. |
| 2,748,773 A | 6/1956 | Vacheresse, Jr. |
| 2,948,222 A | 8/1960 | Pine |
| 3,090,386 A | 5/1963 | Curtis |
| 3,349,772 A | 10/1967 | Rygg |
| 3,372,477 A | 3/1968 | Hoppe |
| 3,374,277 A | 3/1968 | Hoppe |
| 3,393,687 A | 7/1968 | Whitman |
| 3,470,872 A | 10/1969 | Greishaber |
| 3,470,875 A | 10/1969 | Johnson |
| 3,807,407 A | 4/1974 | Schweizer |
| 3,842,840 A | 10/1974 | Schweizer |
| 3,901,244 A | 8/1975 | Schweizer |
| 3,946,740 A | 3/1976 | Bassett |
| 4,164,225 A | 8/1979 | Johnson et al. |
| 4,345,601 A | 8/1982 | Fukuda |
| 4,587,202 A | 5/1986 | Borysko |
| 4,730,615 A | 3/1988 | Sutherland et al. |
| 4,890,615 A | 1/1990 | Caspari et al. |
| 4,950,273 A | 8/1990 | Briggs |
| 4,957,498 A | 9/1990 | Caspari et al. |
| 4,981,149 A | 1/1991 | Yoon et al. |
| 5,059,201 A | 10/1991 | Asnis |
| 5,219,358 A | 6/1993 | Bendel et al. |
| 5,222,962 A | 6/1993 | Burkhart |
| 5,222,977 A | 6/1993 | Esser |
| 5,254,126 A | 10/1993 | Filipi et al. |
| 5,257,637 A * | 11/1993 | El Gazayerli ...... A61B 17/0469 128/898 |
| 5,275,613 A | 1/1994 | Haber et al. |
| 5,312,422 A | 5/1994 | Trott |
| 5,318,577 A | 6/1994 | Li |
| 5,364,408 A * | 11/1994 | Gordon ............. A61B 17/0469 112/169 |
| 5,364,409 A | 11/1994 | Kuwabara et al. |
| 5,387,221 A | 2/1995 | Brisgaard |
| 5,387,227 A | 2/1995 | Grice |
| 5,391,174 A * | 2/1995 | Weston ............. A61B 17/0469 606/148 |
| 5,397,325 A | 3/1995 | Della Badia et al. |
| 5,403,328 A | 4/1995 | Shallman |
| 5,403,346 A | 4/1995 | Loeser |
| 5,454,823 A | 10/1995 | Richardson et al. |
| 5,458,616 A | 10/1995 | Granger et al. |
| 5,462,542 A | 10/1995 | Alesi, Jr. |
| 5,474,565 A | 12/1995 | Trott |
| 5,478,345 A | 12/1995 | Stone et al. |
| D368,776 S | 4/1996 | Toy et al. |
| 5,522,820 A | 6/1996 | Caspari et al. |
| 5,540,704 A | 7/1996 | Gordon et al. |
| 5,562,686 A | 10/1996 | Sauer et al. |
| 5,571,090 A | 11/1996 | Sheds |
| 5,573,542 A | 11/1996 | Stevens |
| 5,613,977 A | 3/1997 | Weber et al. |
| 5,632,751 A | 5/1997 | Piraka |
| 5,649,958 A | 7/1997 | Grimm et al. |
| 5,662,665 A | 9/1997 | Ludwick |
| 5,674,244 A | 10/1997 | Mathys |
| 5,676,675 A | 10/1997 | Grice |
| 5,690,652 A | 11/1997 | Wurster et al. |
| 5,690,653 A | 11/1997 | Richardson et al. |
| 5,704,925 A | 1/1998 | Otten et al. |
| 5,718,714 A | 2/1998 | Livneh |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,797,927 A | 8/1998 | Yoon |
| 5,824,009 A | 10/1998 | Fukuda et al. |
| 5,833,697 A | 11/1998 | Ludwick |
| 5,843,125 A | 12/1998 | Jempolsky |
| 5,860,992 A | 1/1999 | Daniel et al. |
| 5,908,428 A | 6/1999 | Scirica et al. |
| 5,935,149 A | 8/1999 | Ek |
| 5,947,982 A | 9/1999 | Duran |
| 5,972,005 A | 10/1999 | Stalker et al. |
| 5,980,538 A | 11/1999 | Fuchs et al. |
| 6,051,006 A | 4/2000 | Schluzas et al. |
| 6,059,800 A * | 5/2000 | Hart ................ A61B 17/0469 606/139 |
| 6,113,610 A | 9/2000 | Poncet |
| 6,203,895 B1 | 3/2001 | Berger |
| 6,254,620 B1 | 7/2001 | Koh et al. |
| 6,371,963 B1 | 4/2002 | Nishtala et al. |
| 6,530,933 B1 | 3/2003 | Yeung et al. |
| 6,723,107 B1 | 4/2004 | Skiba et al. |
| 6,770,084 B1 | 8/2004 | Bain et al. |
| 6,984,237 B2 | 1/2006 | Hatch et al. |
| D523,554 S | 6/2006 | Weisel |
| D529,173 S | 9/2006 | Weisel |
| 7,112,208 B2 | 9/2006 | Morris et al. |
| D530,421 S | 10/2006 | Topper et al. |
| 7,166,116 B2 | 1/2007 | Lizardi et al. |
| 7,377,926 B2 | 5/2008 | Topper et al. |
| 7,381,212 B2 | 6/2008 | Topper et al. |
| 7,585,305 B2 | 9/2009 | Dreyfuss |
| 2002/0065526 A1 | 5/2002 | Oren et al. |
| 2002/0103493 A1 | 8/2002 | Thal |
| 2002/0138084 A1 | 9/2002 | Weber |
| 2002/0165549 A1 | 11/2002 | Owusu-Akyaw et al. |
| 2003/0065337 A1 | 4/2003 | Topper et al. |
| 2003/0083695 A1* | 5/2003 | Morris .............. A61B 17/0469 606/222 |
| 2003/0176875 A1 | 9/2003 | Anderson et al. |
| 2003/0220658 A1 | 11/2003 | Hatch et al. |
| 2003/0233106 A1 | 12/2003 | Dreyfuss |
| 2004/0010273 A1 | 1/2004 | Diduch et al. |
| 2004/0015177 A1 | 1/2004 | Chu |
| 2004/0249394 A1 | 12/2004 | Morris et al. |
| 2005/0288690 A1 | 12/2005 | Borque et al. |
| 2006/0015125 A1 | 1/2006 | Swain |
| 2006/0276871 A1 | 12/2006 | Lamson |

FOREIGN PATENT DOCUMENTS

| | | |
|---|---|---|
| DE | 4235602 | 4/1994 |
| EP | 0778004 A1 | 12/1995 |

(56) References Cited

FOREIGN PATENT DOCUMENTS

| EP | 0778004 B1 | 12/1995 |
| JP | 1083252 | 3/1989 |
| JP | 7328020 | 12/1995 |
| WO | 9727807 | 8/1997 |
| WO | 0156478 | 8/2001 |
| WO | 03028532 | 9/2002 |
| WO | 2004002324 A1 | 12/2003 |
| WO | 2005107606 | 11/2005 |
| WO | 2007033314 | 3/2007 |

OTHER PUBLICATIONS

An Overview of Nitinol Medical Applications, T. Duerig et al., Elsevier Science S.A., Materials Science & Engineering A273-275 (1999) 149-160.

* cited by examiner

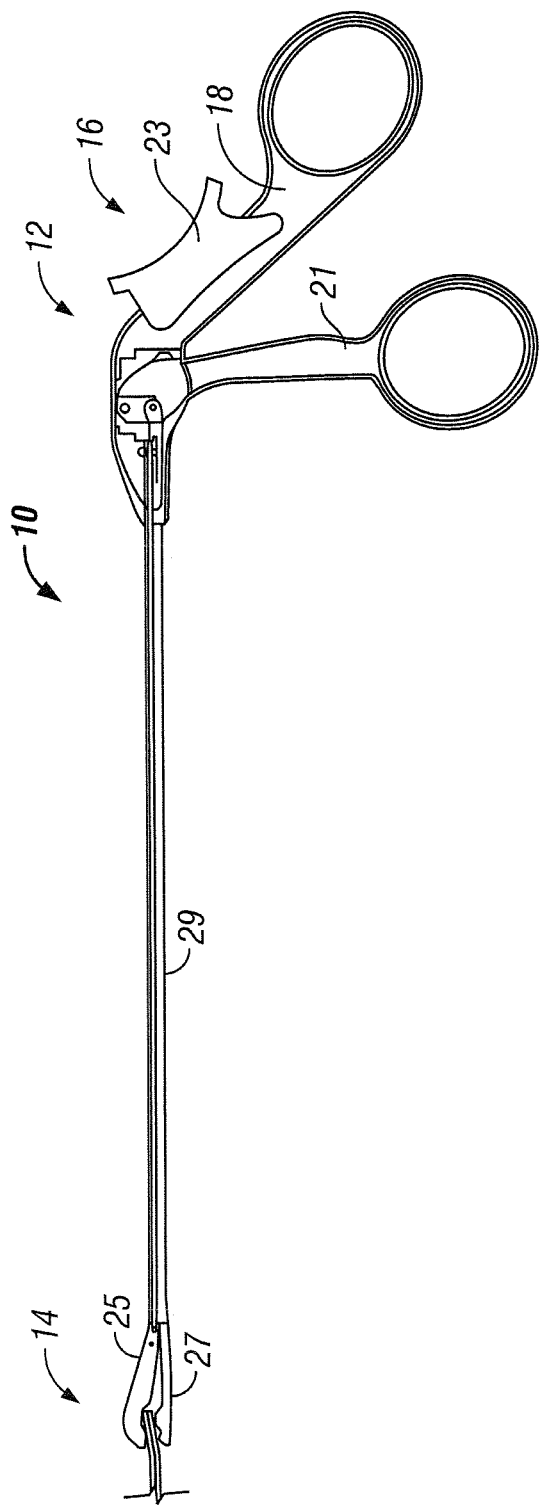
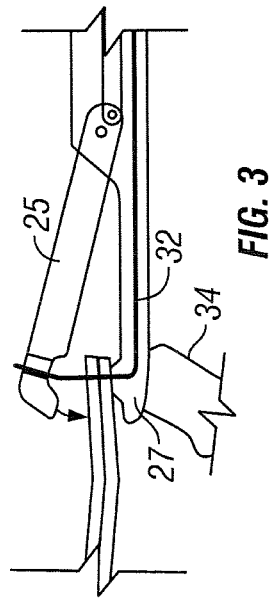
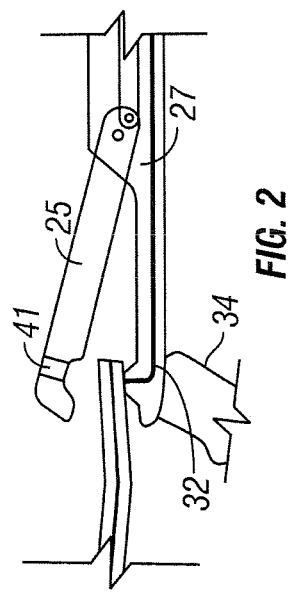
FIG. 1
FIG. 2
FIG. 3

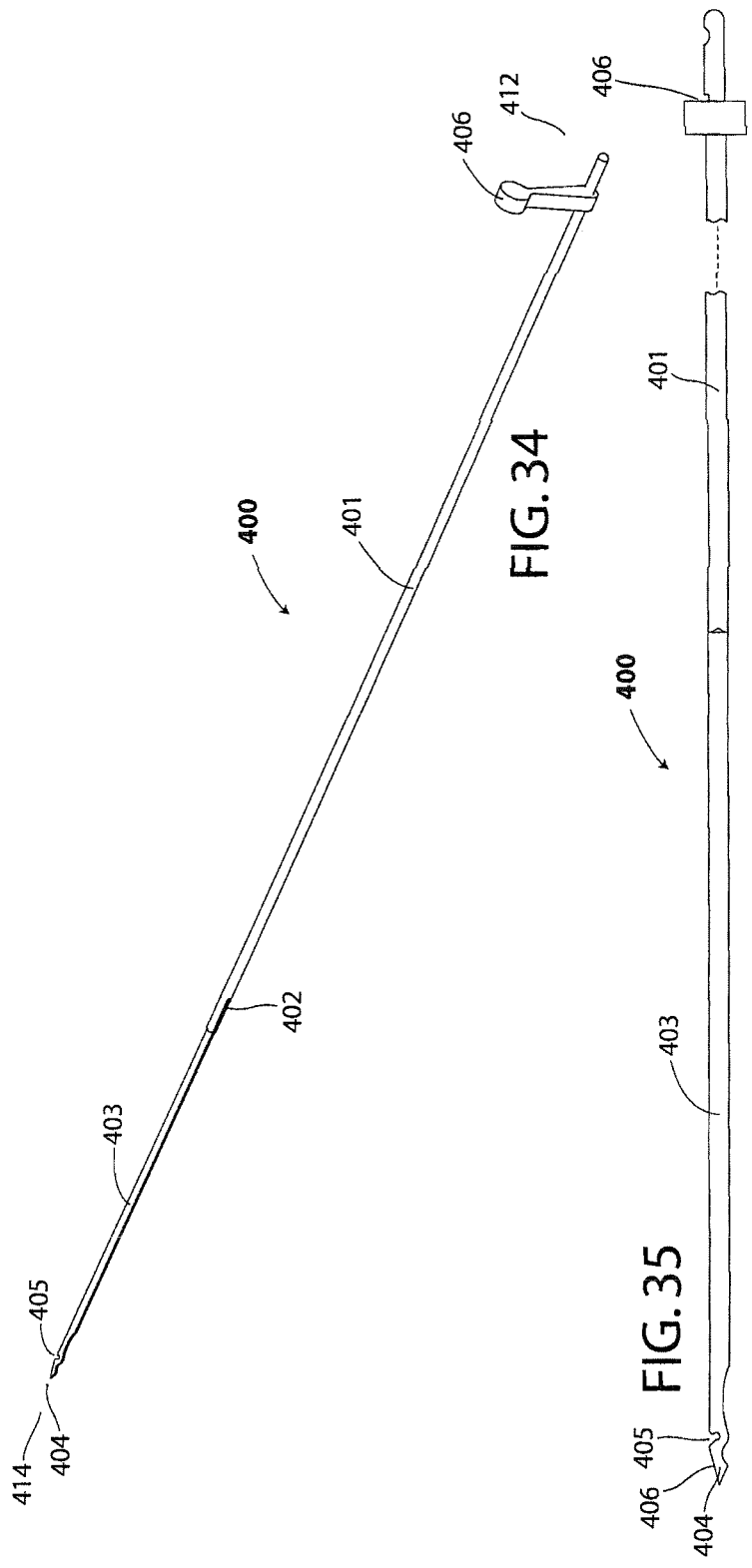

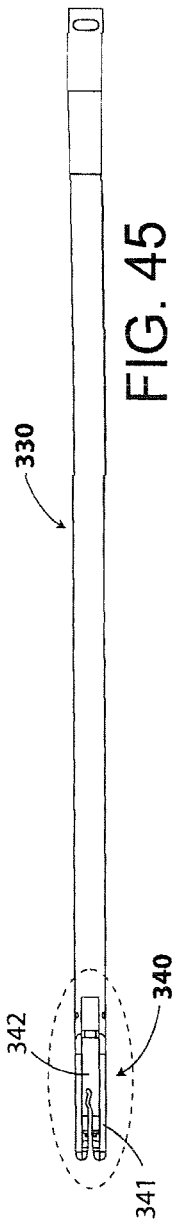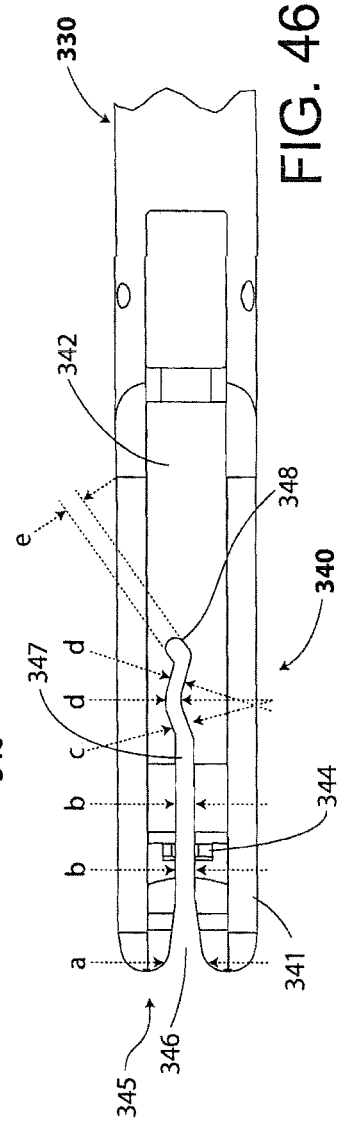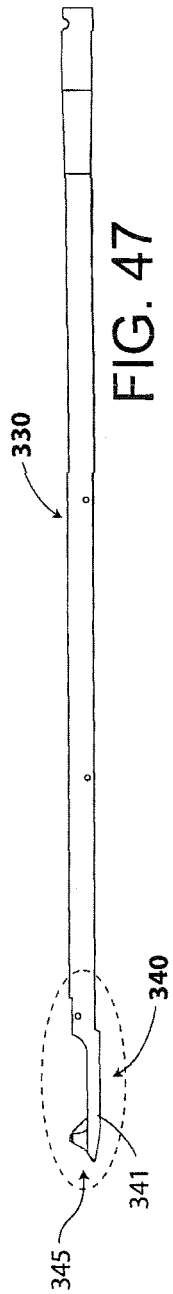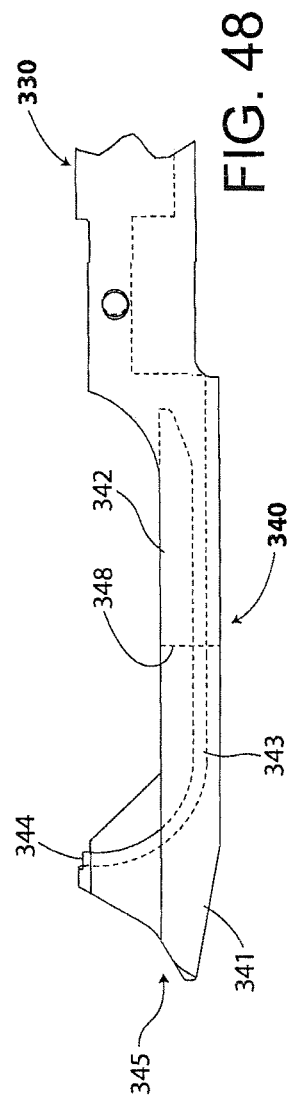
FIG. 45
FIG. 46
FIG. 47
FIG. 48

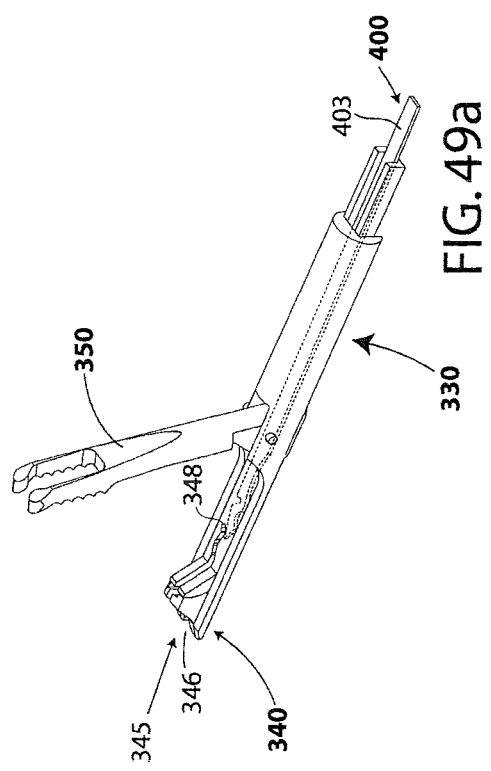
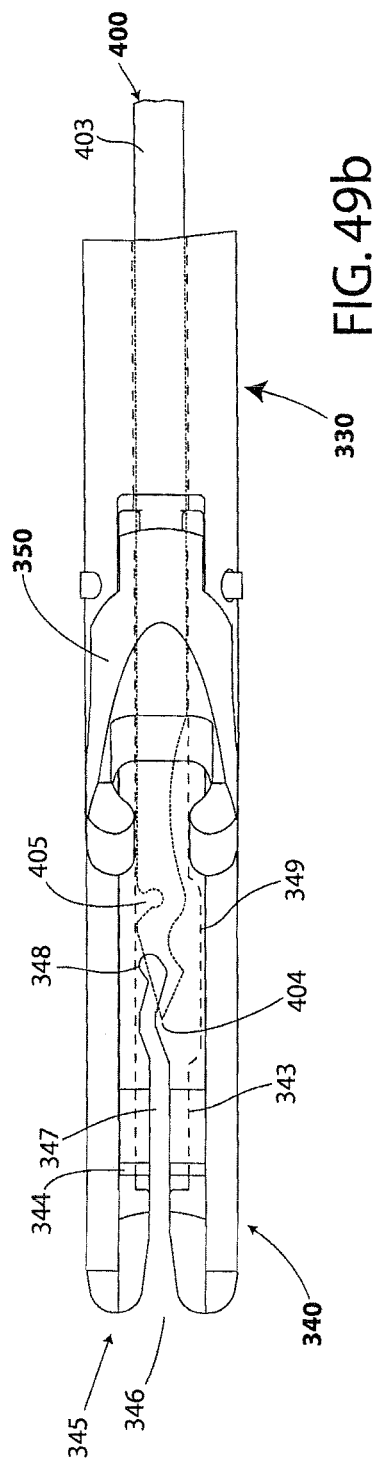

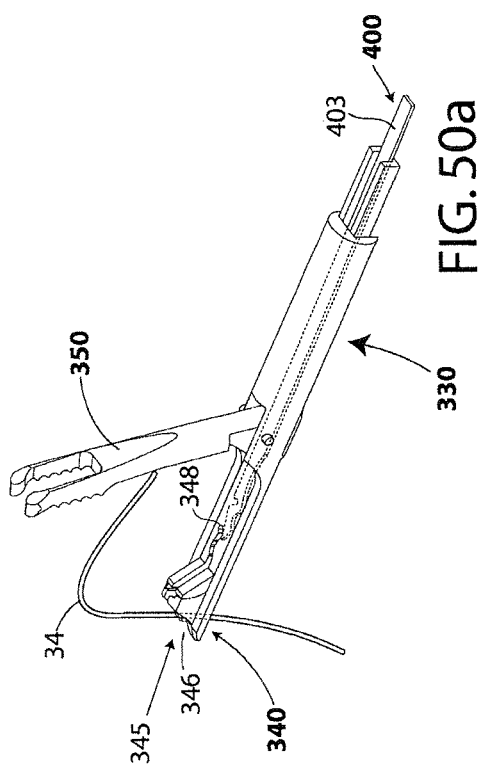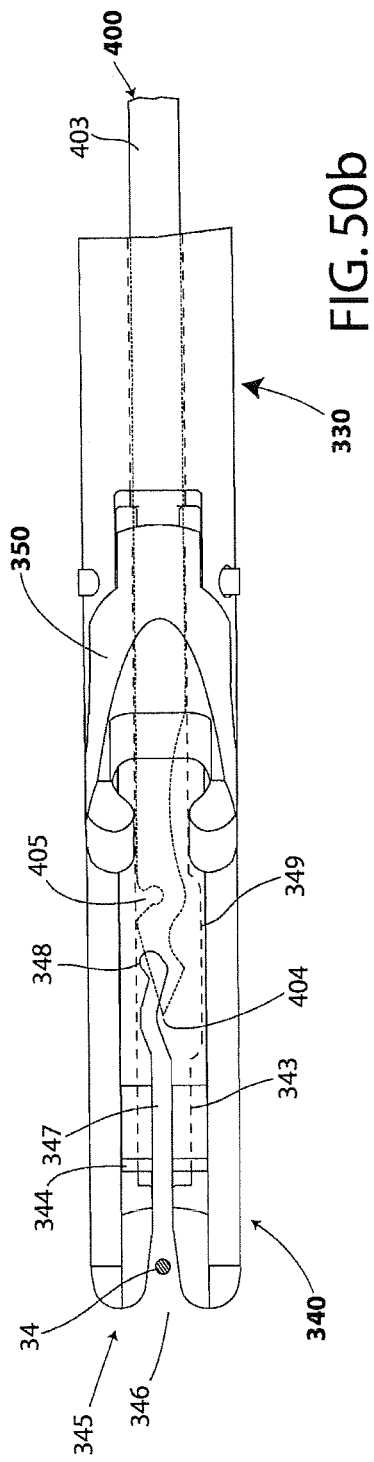
FIG.50a
FIG.50b

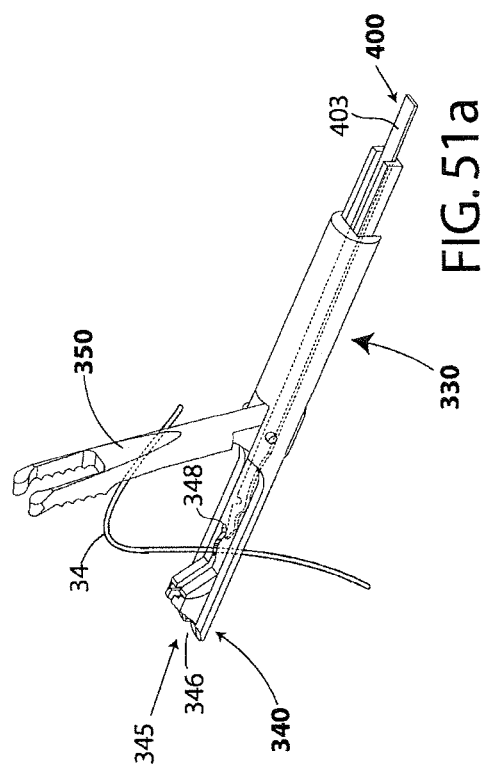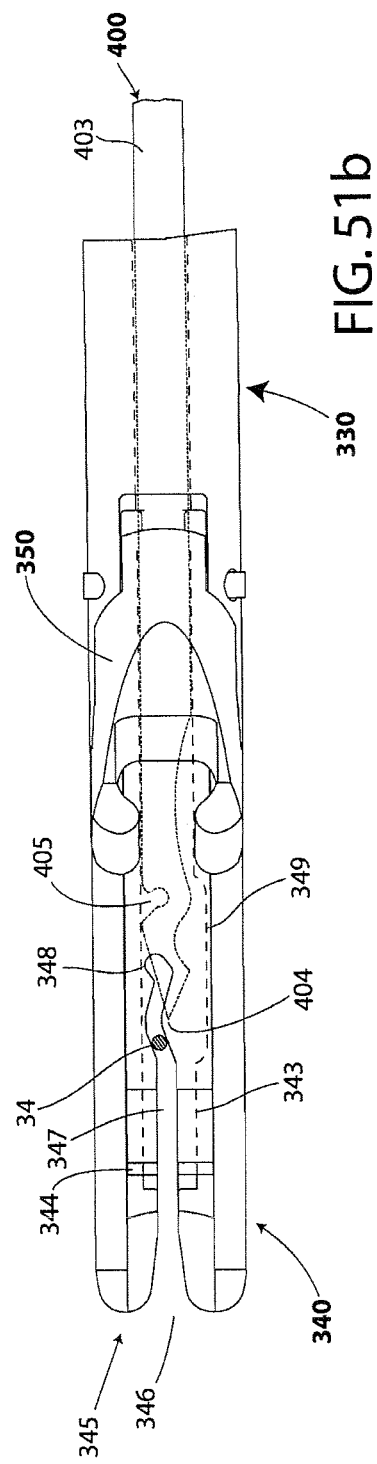

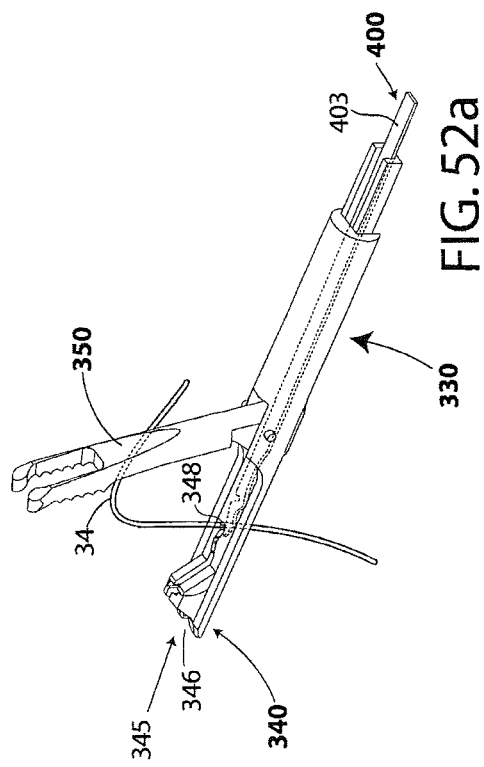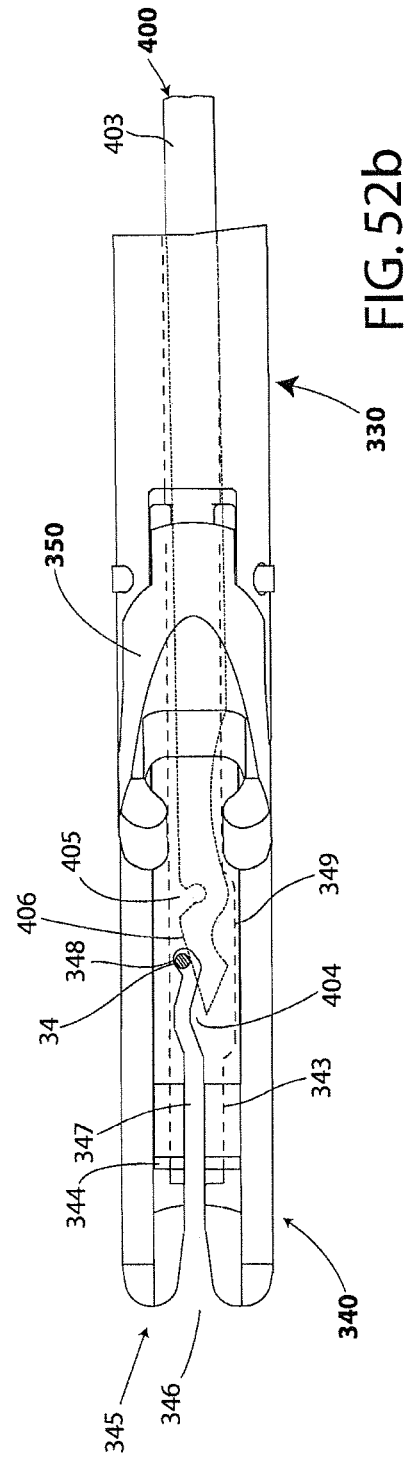

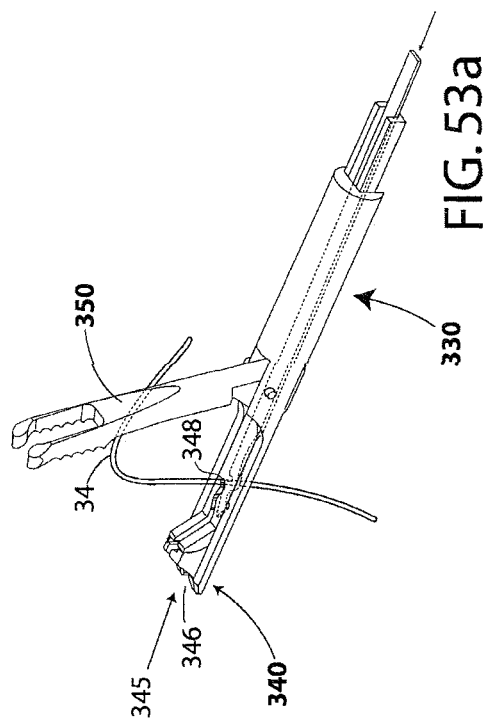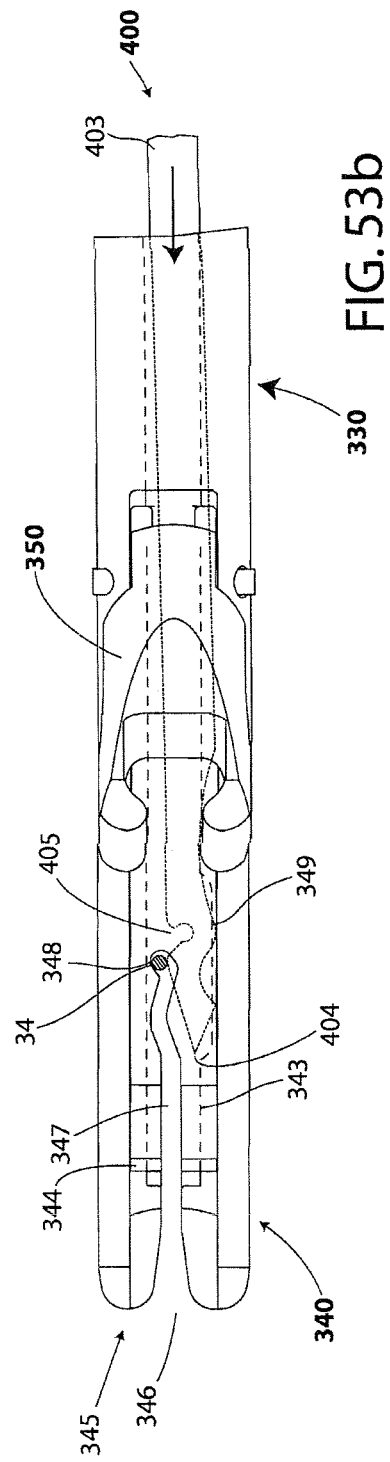

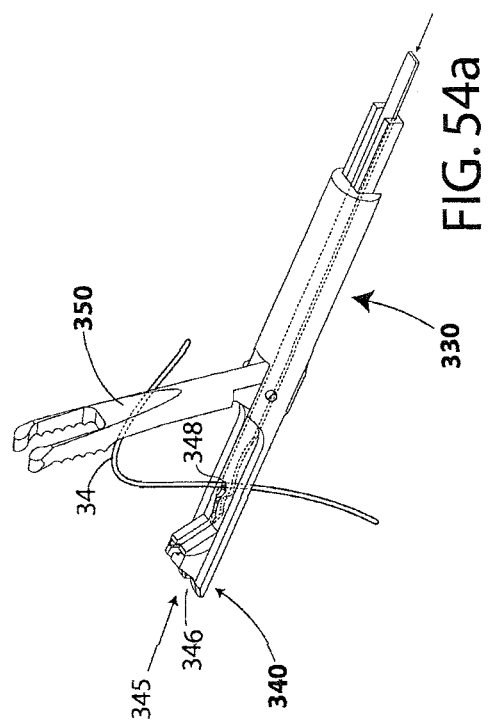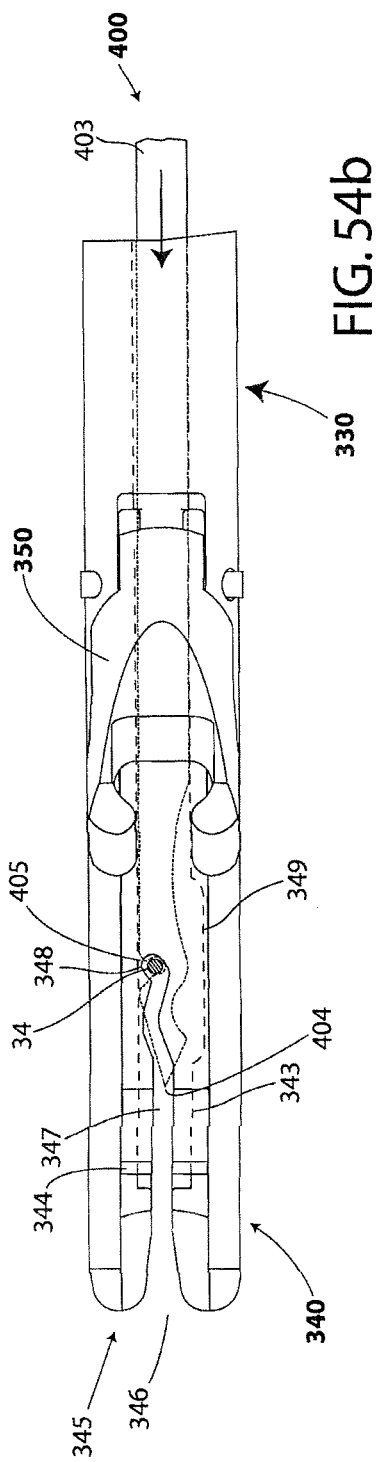

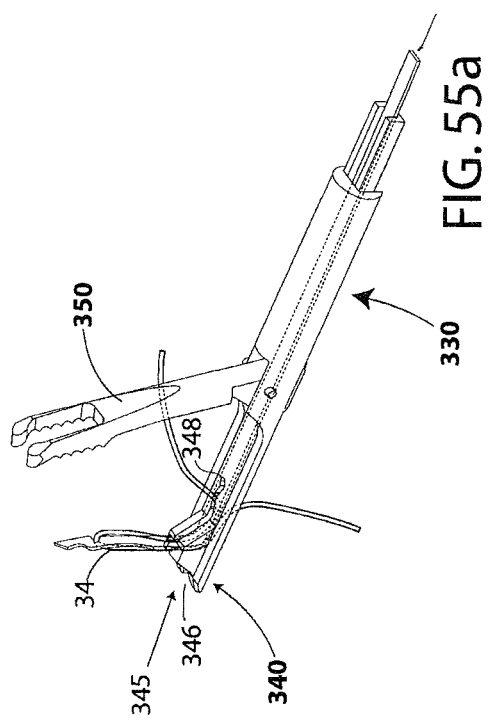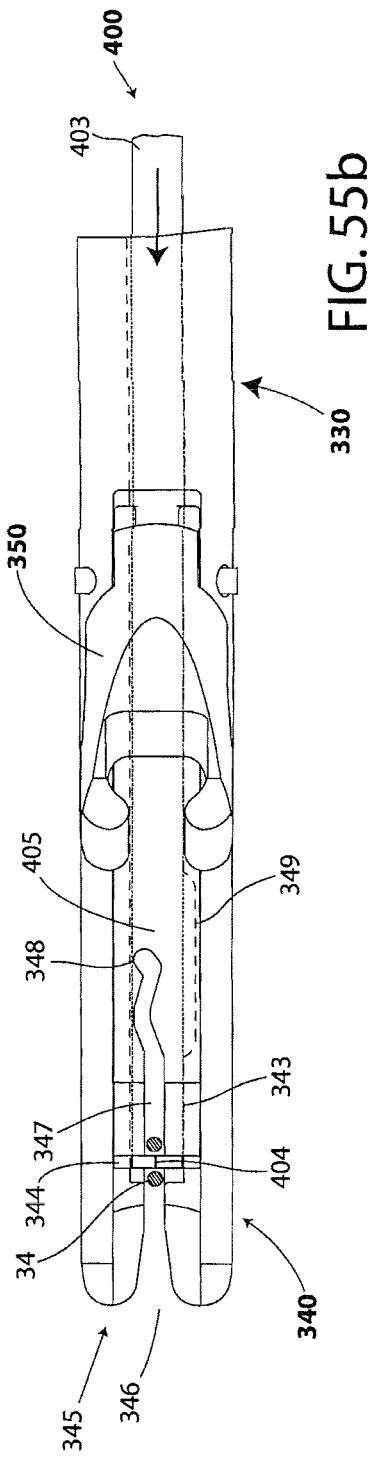

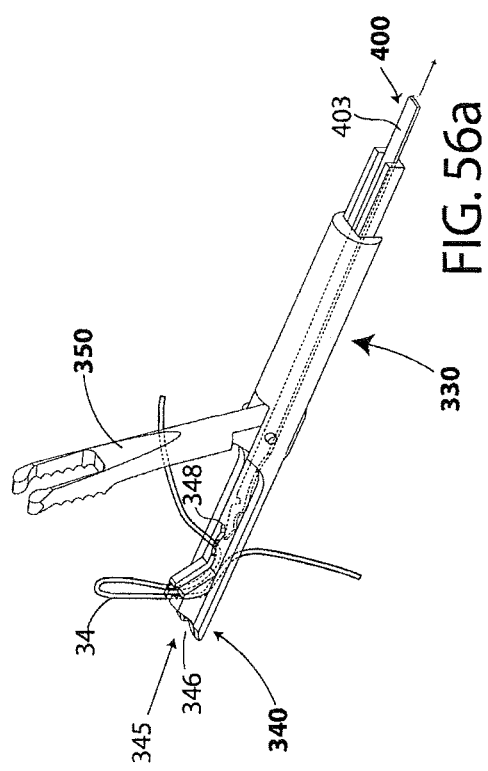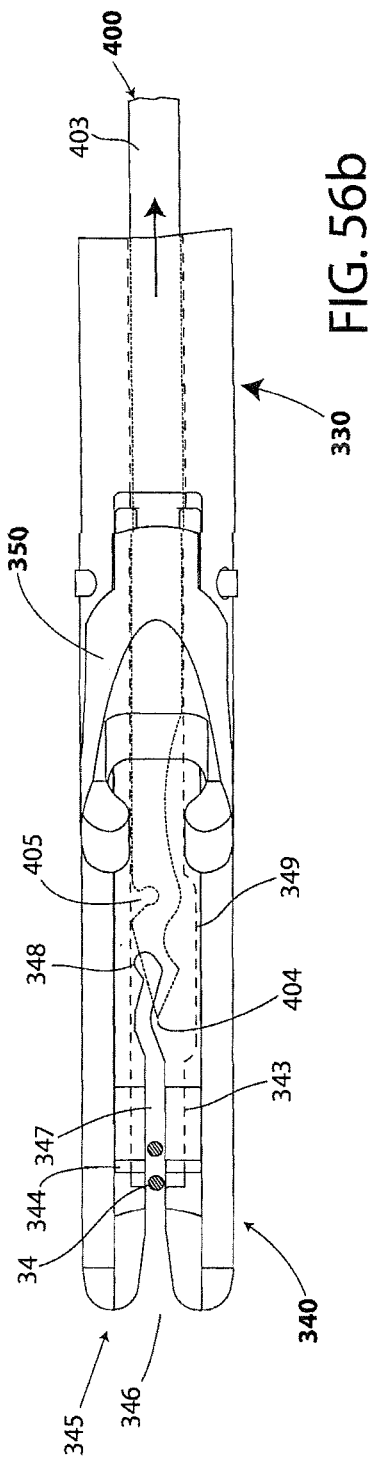

SUTURING APPARATUS AND METHOD

RELATED APPLICATIONS

This application claims priority pursuant to 35 U.S.C. § 120 as a divisional of patent application Ser. No. 14/207,188, filed on Mar. 12, 2014, which application is a continuation of patent application Ser. No. 13/855,900, filed on Apr. 3, 2013, now issued as U.S. Pat. No. 9,808,241, which application is a divisional of patent application Ser. No. 12/971,457, filed Dec. 17, 2010, now issued as U.S. Pat. No. 8,540,732, which application is a divisional of U.S. patent application Ser. No. 11/738,129, filed Apr. 20, 2007, now issued as U.S. Pat. No. 7,879,046, which application is a continuation-in-part of U.S. patent application Ser. No. 10/255,523, filed Sep. 25, 2002, entitled "SUTURING APPARATUS AND METHOD," now issued as U.S. Pat. No. 7,377,926, which application relates to and claims priority pursuant to 35 U.S.C. § 119(e) from U.S. Provisional Application Ser. No. 60/326,287, filed on Oct. 1, 2001, entitled "SUTURING APPARATUS AND METHOD", and also from U.S. Provisional Application Ser. No. 60/358,960, filed on Feb. 25, 2002, entitled "SUTURING APPARATUS WITH RETAINING MECHANISM." Benefits of priority of these applications, including the filing dates of Oct. 1, 2001, Feb. 25, 2002, and Sep. 25, 2002, are hereby claimed, and their disclosures are hereby incorporated by reference as if fully set forth herein.

BACKGROUND OF THE INVENTION

1. Field of the Invention

The invention relates generally to suturing devices and methods.

2. Description of Prior Art and Related Information

Suturing apparatus in the past have been required to have an elongate configuration and a low profile facilitating their use through cannulas in less invasive surgery. These devices have typically included opposing jaws which clamp on to the tissue to be sutured. Beyond this simple clamping motion, typically facilitated by scissor handles, the mechanism for threading a suture between the jaws and through the tissues have been exceedingly complex.

This complexity has derived primarily from the fact that the elongated, low profile configuration calls for an operating force that can be transmitted through an elongate tube. This force along the axis of the instrument must then be converted into a force extending generally perpendicular to the axis between the jaws. No simple structure has been devised to accommodate this transition. Furthermore, loading a suture onto a mechanism has also been complicated due to the complexity of the suturing mechanisms.

SUMMARY OF THE INVENTION

In accordance with the present invention, structures and associated methods are disclosed which address these needs and overcome the deficiencies of the prior art.

In one aspect, a suturing apparatus comprises a first jaw and a second jaw movable with respect to each other. A bendable needle is carried by the first jaw and adapted to carry a suture. The needle is movable between a first position wherein the needle is substantially housed within the jaw and a second position wherein a distal portion of the needle protrudes from the first jaw. The apparatus further comprises means for securing the suture in place prior to being carried by the bendable needle, and a suture receiver spaced apart from the first jaw and configured to disengage the suture carried by the bendable needle.

The securing means may comprise a cantilevered spring included in a distal portion of the first jaw, a groove defined in a distal portion of the first jaw, a flap, or an elastomeric pad. The first jaw defines an axis and further comprises a transition block adapted to guide the bendable needle in a direction substantially perpendicular to the axis.

In another aspect, a suturing apparatus comprises a first jaw defining an ingress, a second jaw movable with respect to the first jaw, and a bendable needle carried by the first jaw and movable between a proximal position and a distal position. The needle defines a needle slot that may be aligned with the ingress to enable loading of a suture through the ingress into the needle slot.

The apparatus further comprises a suture receiver which may be disposed adjacent to the second jaw, or integral with the second jaw. The apparatus further comprises an actuator coupled to the bendable needle and configured for moving the bendable needle between the proximal position and the distal position. The actuator preferably comprises a thumb lever. The first jaw defines an axis and further comprises an axial slot in communication with the ingress. The ingress may comprise a lateral opening, and the needle slot may comprise a lateral slot.

A suture retrieving apparatus is also provided. The suture retrieving apparatus comprises a first jaw and a second jaw movable with respect to each other, a suture receiver spaced apart from the first jaw, the suture receiver being adapted to releasably retain a suture, and a bendable needle carried by the first jaw. The bendable needle is movable between a proximal position and a distal position. The bendable needle has a distal needle portion adapted to engage with the suture when the bendable needle is in the distal position. The distal needle portion comprises a hook. The second jaw may comprise the suture receiver.

A method is provided for suturing a tissue. The method comprises the steps of clamping a piece of tissue to be sutured, securing a suture in place for engagement with a bendable needle, engaging a suture with a bendable needle, carrying the suture toward a receiver with the bendable needle, retaining the suture with the receiver, and retracting the bendable needle to release the suture.

The step of clamping a tissue to be sutured comprises the step of capturing the piece of tissue with a first jaw and a second jaw. The method further comprises the step of advancing the bendable needle in an axial direction.

The step of carrying the suture toward a receiver with the bendable needle comprises the step of bending the bendable needle, and moving at least a portion of the bendable needle in a transverse direction.

A method is also provided for loading a suture onto a suturing apparatus. The method comprises the steps of housing a needle with a needle slot in a first jaw, biasing the needle in a distal direction with respect the first jaw so that the needle slot is not aligned with an ingress of the first jaw, aligning the needle slot with the ingress, disposing a suture through the ingress into the needle slot, and releasing the biased needle such that the needle engages the suture and carries the suture distally.

The step of aligning the needle slot with the ingress may comprise the step of moving the needle either proximally or distally. The step of moving the needle proximally comprises moving the needle proximally with a finger slide. The step of disposing a suture through the ingress into the needle slot comprises looping the suture about the ingress.

In summary, a suturing apparatus comprises a pair of jaws. A bendable needle housed in one of the jaws is adapted to carry a suture toward a suture receiver disposed adjacent to the opposite jaw. A transition block curves the needle and directs it in a direction generally not parallel to an axis of the carrying jaw. The needle may also be configured to retrieve a suture. A retaining mechanism holds a suture in place to be engaged by the needle. The jaw housing the needle may include a lateral opening through which the suture may be inserted. The needle may also include a lateral notch which may be aligned with lateral opening to receive the suture. An actuator coupled to the needle enables the user to move the needle proximally to align the notch with the lateral slot.

In another aspect, a suturing apparatus comprises a proximal handle and an elongated distal shaft having a distal end; a grasping mechanism positioned adjacent to the distal end, the grasping mechanism including a top jaw and a bottom jaw, at least one of the top jaw and the bottom jaw hinged to the shaft at a position proximal to the distal end, the grasping mechanism operationally coupled to the handle for opening and closing the top jaw and the bottom jaw with respect to one another at the distal end; a slot extending vertically through the top jaw and the bottom jaw and extending proximally from the distal end to a slot end within at least one of the top jaw and the bottom jaw, the slot having a slot width tapering proximally toward the slot end for frictionally retaining an intermediate portion of a length of suture; and a suture needle longitudinally positionable within and distally deployable from the shaft, the needle having a open-sided notch engageable with the intermediate portion of suture, for passing the suture when the needle is deployed from the shaft, the needle operationally coupled to the handle for positioning and deployment.

In another aspect, a suturing apparatus comprises a ratchet that locks unless positive disabled. In a preferred embodiment, such a suturing apparatus comprises a proximal handle and an elongated distal shaft having a distal end; a grasping mechanism positioned adjacent to the distal end, the grasping mechanism including a top jaw and a bottom jaw, at least one of the top jaw and the bottom jaw hinged to the shaft at a position proximal to the distal end for movement between an open position and a closed position; a jaw movement mechanism that operationally couples the grasping mechanism to the handle for opening and closing the top jaw and the bottom jaw with respect to one another at the distal end; a spring that biases grasping mechanism to the open position; and a ratchet latch assembly that prevents the jaw movement mechanism from moving toward the open position unless positive action is taken to disable the ratchet latch assembly.

In another aspect, a suturing apparatus comprises a needle movement mechanism that moves the needle distally when the needle movement mechanism is moved proximally. In a preferred embodiment, such a suturing apparatus comprises a bendable needle having a generally flat, narrow and elongate configuration, and a distal needle tip; a first jaw defining an axis and a needle channel that guides the bendable needle along the needle channel to a channel exit; a second jaw movable with respect to the first jaw for holding tissue to be sutured between the first and second jaws; the bendable needle reciprocally movable between a proximal needle position where the needle tip is resting inside the first jaw and a distal needle position where the needle tip is protruding from the first jaw; and a needle movement mechanism comprising a needle trigger that reciprocally moves between a distal trigger position and a proximal trigger position, the needle trigger operatively connected to the bendable needle to move the bendable needle distally when the needle trigger is pulled proximally.

In another aspect, a suturing apparatus comprises a needle that automatically returns to a loading position. In a preferred embodiment, such a suturing apparatus comprises a handle assembly; an elongate shaft extending from a distal end of the handle assembly; a first jaw extending distally from the elongate shaft, the first jaw having an axis, a needle channel, a channel exit, and a suture loading ingress; a second jaw movable with respect to the first jaw for holding tissue to be sutured between the first and second jaws; a bendable needle having a generally flat, narrow and elongate configuration, a distal needle tip, and an open-sided needle notch, the bendable needle reciprocally movable between a proximal needle position where the needle tip and open-sided needle notch are resting inside the first jaw and the suturing apparatus is ready for suture to be loaded into the first jaw via the suture loading ingress and a distal needle position where the needle tip and open-sided needle notch are protruding from the first jaw with the suture loaded into the first jaw via the suture loading ingress located on an opposite side of the tissue in the open-sided needle notch; a needle movement mechanism that reciprocally moves the needle distally and proximally between the proximal needle position and the distal needle position; and a spring that automatically returns the bendable needle to the proximal needle position and readies the suturing apparatus for suture to be loaded into the first jaw via the suture loading ingress.

In another aspect, a suturing apparatus comprises a means for loading suture in a single step. In a preferred embodiment, such a suturing apparatus comprises a handle assembly; an elongate shaft extending distally from the handle assembly; a first jaw extending distally from the elongate shaft, the first jaw having an axis, a top, a bottom, a needle channel that runs along the first jaw's axis and around a curve to a channel exit, and a suture loading ingress that extends through the first jaw from the top to the bottom and leads to a suture channel that also extends through the first jaw from the top to the bottom, the suture channel being in communication with and in substantial alignment with the needle channel; a second jaw movable with respect to the first jaw for holding tissue to be sutured between the first and second jaws; a bendable needle having a generally flat, narrow and elongate configuration, a distal needle tip, and an open-sided needle notch, the bendable needle reciprocally movable between a proximal needle position where the needle tip and open-sided needle notch are resting inside the first jaw and the suturing apparatus is ready for suture to be loaded into the first jaw via the suture loading ingress and a distal needle position where the needle tip and open-sided needle notch are protruding from the first jaw with the suture loaded into the first jaw via the suture loading ingress located on an opposite side of the tissue in the open-sided needle notch; and means for retaining suture loaded into the first jaw via the suture loading ingress prior to deployment of the bendable needle, the suture being loaded into the first jaw in a single step without regard to the position of the bendable needle and its open-sided needle notch.

In yet another aspect, a novel suturing needle comprises a needle with a proximal end and a distal end, with at least a distal portion of the needle formed from a bendable material having a generally flat, narrow and elongate configuration, and with a sharp needle tip located at a distal end of the distal portion; and a finger tab connected to the bendable needle at or near a proximal end of the needle for loading the needle into the surgical suturing device.

In yet another aspect, a novel suturing needle comprises a needle with a proximal end and a distal end, with at least a distal portion of the needle formed from a bendable material having a generally flat, narrow and elongate configuration, and with a sharp needle tip located at a distal end of the distal portion; and a lubricious coating applied to a surface of the needle to reduce a force required to slide the needle back and forth within the surgical suturing device or tissue to be sutured.

In yet another aspect, a novel method for loading suture in a single step is provided for suturing a tissue. The method comprises loading the suture into the suture channel via the suture loading ingress such that the protrudes from the top and bottom of the first jaw and extends across the needle channel; retaining the suture in the suture channel prior to deployment; and capturing the retained suture with the bendable needle as the bendable needle is moved distally during deployment.

The invention, now having been briefly summarized, may be better visualized by turning to the following drawings wherein like elements are referenced by like numerals.

BRIEF DESCRIPTION OF THE DRAWINGS

FIG. 1 is a side elevation view of a first preferred embodiment of a suturing apparatus according to the invention;

FIG. 2 is a close-up view of the first preferred suturing apparatus showing a bendable needle substantially housed within a lower jaw;

FIG. 3 is a close-up view of the first preferred suturing apparatus showing the bendable needle piercing a piece of tissue;

FIG. 34 is a perspective view of a bendable needle for use with the suture passing apparatus of FIG. 33;

FIG. 35 is a top plan view of the bendable needle of FIG. 34;

FIG. 36 is a left side view of the bendable needle of FIG. 34;

FIG. 45 is a top plan view of the fixed jaw at the distal end of the shaft of suture passing apparatus;

FIG. 46 is an enlarged close-up at the distal tip of FIG. 45;

FIG. 47 is side view of the fixed jaw at the distal end of the shaft of suture passing apparatus;

FIG. 48 is an enlarged close-up at the distal tip of FIG. 47; and

FIGS. 49a and 49b to 56a and 56b are successive pairs of a perspective and top plan view of the distal end of the preferred embodiment, respectively, illustrating the overall operation from the loading of the suture through the end slot, the forward translation and momentary sideways movement of the needle as it engages the suture, the creation of a suture loop, and the retraction of the needle to the resting position.

Figure 4:
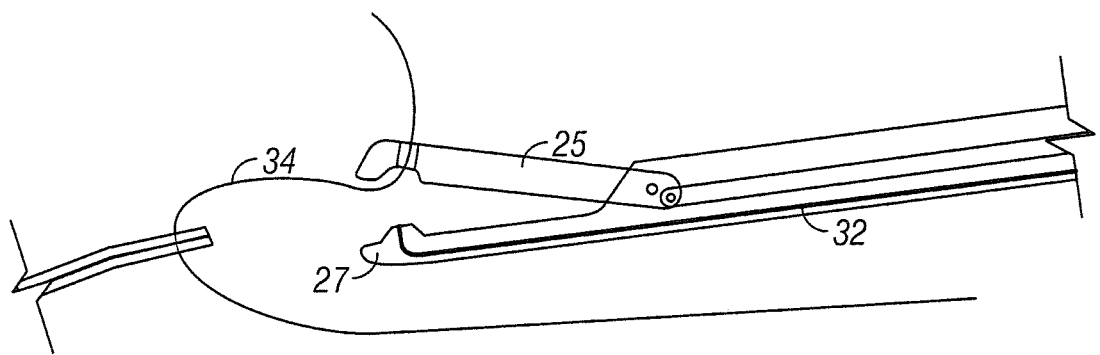
FIG. 4 is a close-up view of the first preferred suturing apparatus removed from the piece of tissue.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

A first preferred embodiment of a suturing apparatus is illustrated in FIG. 1 and designated generally by the reference numeral 10. The apparatus 10 is illustrated to have an elongate configuration with a proximal end 12 and a distal end 14. A handle assembly 16 is disposed at the proximal end 12 and includes scissor handles 18 and 21 as well as an actuator 23. A pair of opposing jaws 25 and 27 are disposed at the distal end and are coupled to the handle assembly 16 through an elongate shaft or tube 29. In one embodiment, the upper jaw 25 is pivotal with respect to the lower jaw 27 as illustrated in FIG. 2.

In the illustrated embodiment the lower jaw 27 includes a needle 32 of particular interest to the present invention. In this case, the needle 32 includes a body having a generally flat, narrow and elongate configuration. As shown in FIGS. 1-3, the needle 32 is formed from a bendable material so that it can be moved generally with an axial force provided, for example, by a user's thumb, and can be bent on a curve, for example, to 90°, to move generally perpendicular to the axis and toward the opposing upper jaw 25. It is to be expressly understood that the needle 32 can be substantially straight, as shown in FIG. 1, and then be bent at any angle and advanced in any direction away from the axis. The actuator 23, which preferably comprises a thumb rocker or slide, is coupled to the needle 32. The actuator 23 enables a user to advance the needle 32 distally to a protruding, operative position and proximally to a retracted, inoperative position.

Threading this needle 32 with a suture 34 enables the needle to be deployed through the tissue and to carry with it the suture 34 to be threaded. The opposing jaw 25 may include an optional receiver which is adapted to remove the suture from the needle 32 as the needle 32 is withdrawn back into the lower jaw 27. At this point, the suture extends through the tissue and into the upper jaw. Removal of the jaws from the tissue, as illustrated in FIG. 4 permits withdrawal of the apparatus 10 leaving the suture in place for tying or further manipulation. A suture receiver is optional since the tissue itself may frequently serve as a receiver for the suture once the needle is retracted.

Figure 5A:
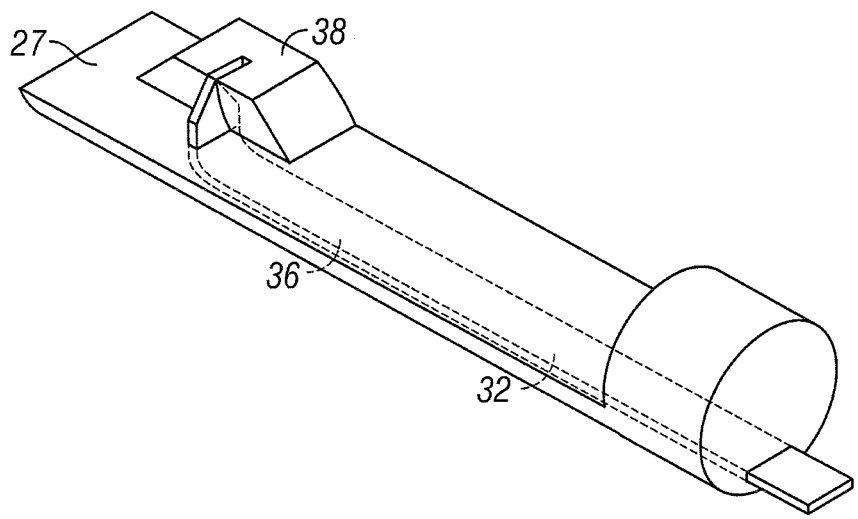
FIG. 5A is a perspective view of a jaw of the first preferred suturing apparatus housing the bendable needle.
Figure 5B:
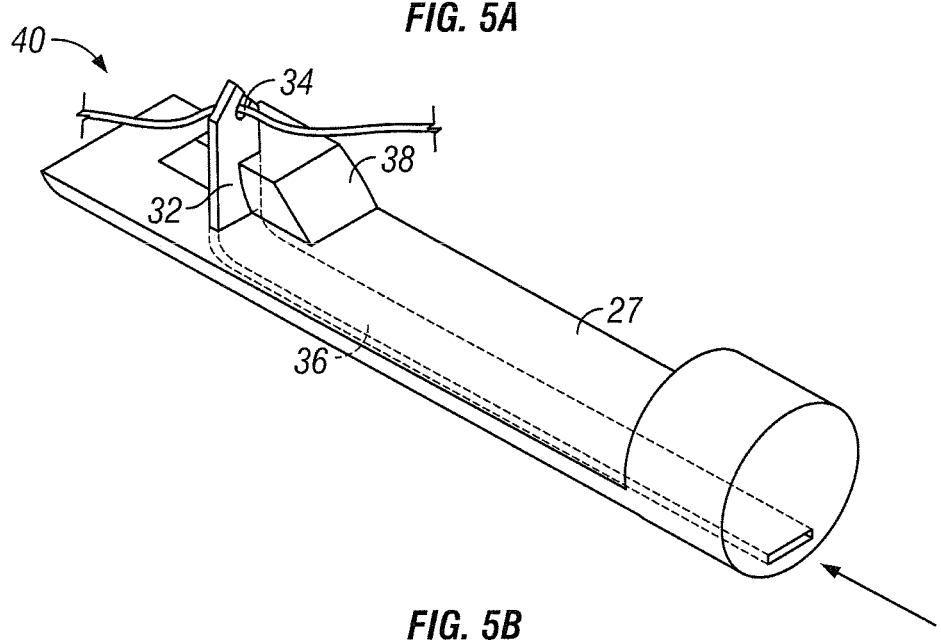
FIG. 5B is a perspective view of the jaw of FIG. 5A showing the bendable needle advanced to a distal, piercing position.

In this embodiment, the lower jaw is illustrated in FIG. 5A to include an elongate configuration and a channel 36 adapted to receive the needle 32. The needle is bent at the distal end of this jaw 27 and up through a transition block 38 which aides in curving the needle 32 and directing it toward a suture receiver. Though the illustrated embodiment shows the transition block 38 curving the needle 32 perpendicularly with respect to the axis of the lower jaw 27, the transition block 38 may be configured to curve and direct the needle 32 at any particular angle or direction that is generally unparallel to the axis of the lower jaw 27. FIG. 5A shows the needle retracted and FIG. 5B shows the needle 32 deployed and provided with a slot 40 to carry the suture 34 to the opposing jaw 25. This configuration is further illustrated in the radial cross-section view of FIG. 6.

Figure 7A:
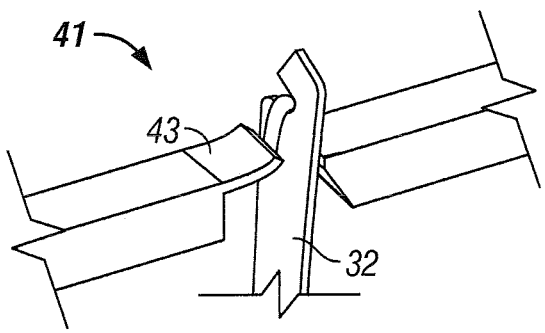
FIG. 7A is an operative view illustrating a preferred suture receiver intercepting the suture carried by the needle.
Figure 7B:
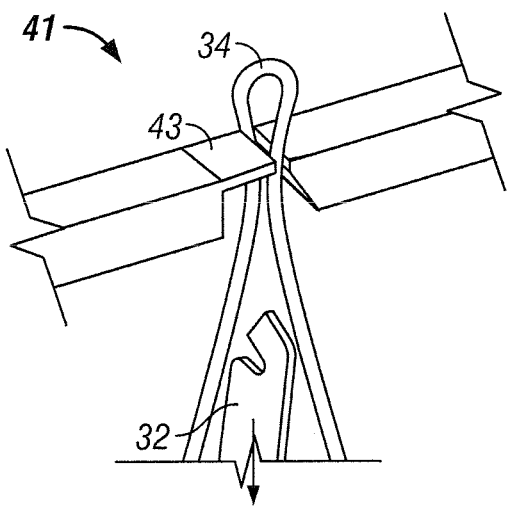
FIG. 7B is a perspective view of the preferred suture receiver of FIG. 7A retaining the suture after the needle is retracted.

In the upper jaw 25, a suture receiver 41 is provided to remove the suture 34 from the needle 32. A metal or elastomeric flap, or paddle, 43 is provided to engage the needle 32 and threaded suture 34 as illustrated in FIG. 7A. This flap 43 forces the suture 34 from the needle slot 40 as the needle 32 is withdrawn as illustrated in FIG. 7.

Figure 8A:
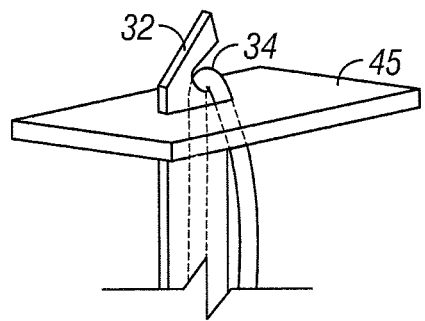
FIG. 8A is an operative view of a further preferred suture receiver.
Figure 8B:
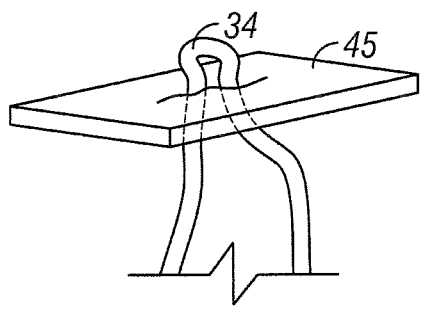
FIG. 8B is an operative of the preferred suture receiver of FIG. 8A retaining the suture after the needle is retracted.

In a similar embodiment, the needle 32 and threaded suture 34 is forced through an elastomeric pad 45 which similar engages the suture 34 and removes it from the needle slot 40 as the needle 32 is withdrawn as illustrated in FIG. 8B.

Figure 6:
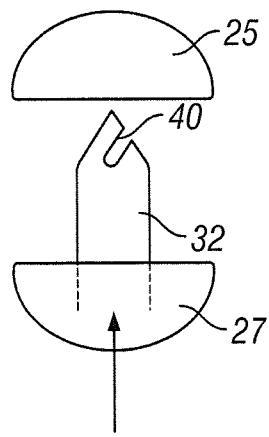
FIG. 6 is a front end view of the first preferred suturing apparatus.
Figure 9:
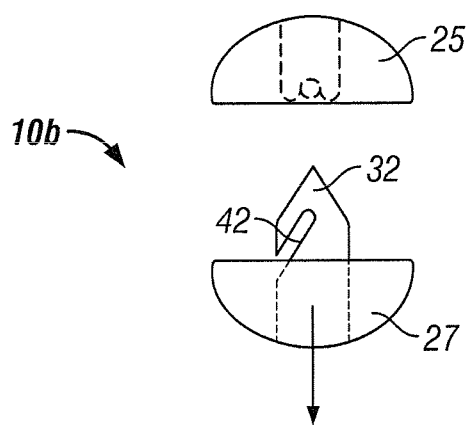
FIG. 9 is a front end view of a second preferred embodiment of a suture apparatus comprising a suture retrieving device.
Figure 10A:
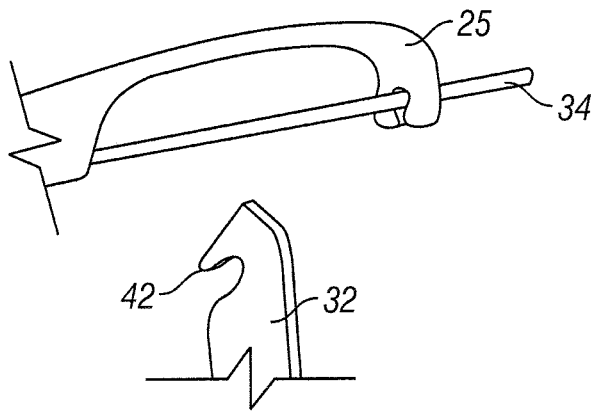
FIG. 10A is an operative view of the preferred suturing retrieving device of FIG. 9.
Figure 10B:
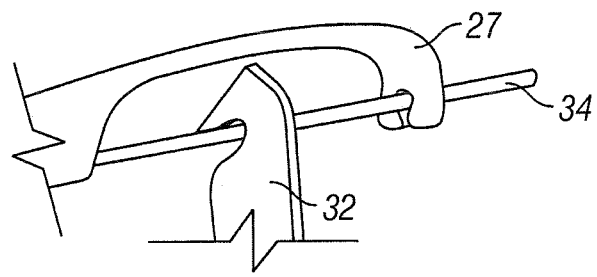
FIG. 10B is an operative view of the preferred suturing retrieving device showing a retrieving needle engaging a suture.
Figure 10C:
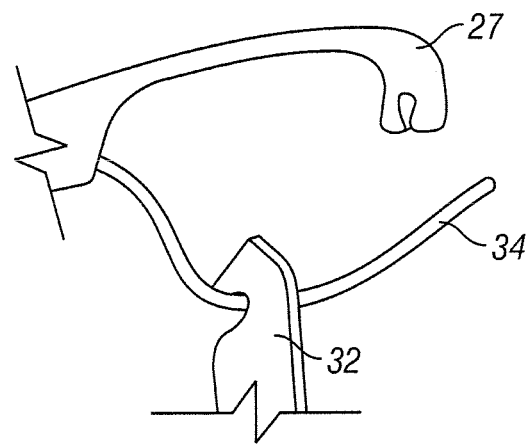
FIG. 10C is an operative view of the preferred suturing retrieving device showing the needle retrieving the suture.

A second preferred embodiment of a suturing apparatus is illustrated in FIG. 9 which is a cross-section view similar to FIG. 6, but showing a needle 32 which functions as a retriever rather than a carrier. In this embodiment, the suture 34 is initially carried by the upper jaw 25. A needle slot 42 in this case extends distally from the side of the needle 32. When this needle 32 and slot 42 are extended, as illustrated in FIG. 10A, the slot 42 engages the suture 34 in the upper jaw 25. As the needle 32 is withdrawn, the suture is retrieved in the needle slot 42 and carried back through the tissue. The final step in this process is the same as previously discussed with reference to FIG. 4.

Figure 11:
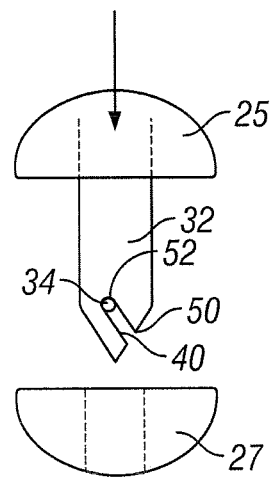
FIG. 11 is a front end view of a third preferred suturing apparatus wherein a bendable needle is carried by an upper jaw.

It will be apparent that this apparatus 10 could also operate with the needle 32 carried by the upper jaw 25. Such a feature is shown in a third preferred embodiment illustrated in the cross-sectional view of FIG. 11 where the needle 32 functions as a suture carrier. In particular, a suture slot 40 defined in the needle 32 comprises an opening 50 that is located distally to an end 52 such that the slot 40 faces the receiver, or lower jaw 27. A suture 34 is thus carried by the needle 32 toward the opposing, lower jaw 27.

Figure 12:
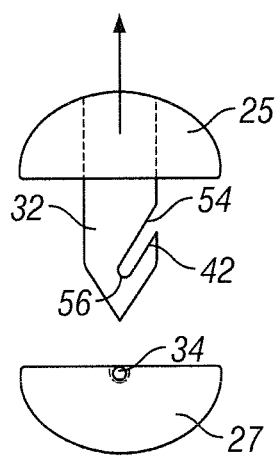
FIG. 12 is a front end view of a fourth preferred suture retrieving apparatus wherein a bendable needle is carried by an upper jaw.

In FIG. 12, a fourth preferred embodiment of a suturing apparatus comprises a suture retrieving device wherein the needle 32 is carried by the upper jaw 25. In this case, the needle 32 functions as a retriever of the suture 34. The needle 32 defines a slot 42 with an opening 54 that is located proximally to an end 56 such that the slot 42 faces away from the opposing, lower jaw 27. In the illustrated embodiment, a distal portion of the needle 32 is thus preferably shaped as a hook.

Figure 13:
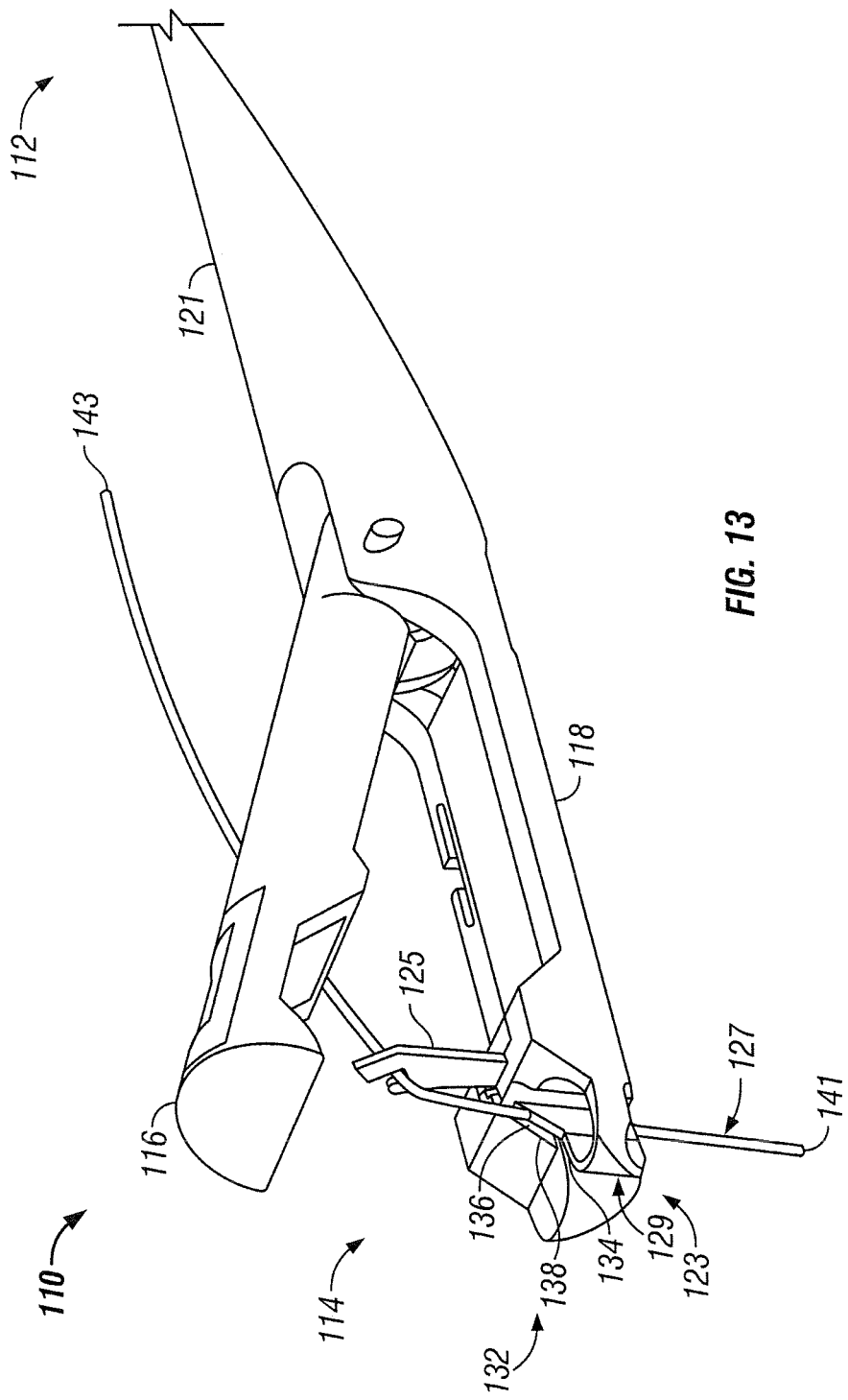
FIG. 13 is a perspective view of a fifth preferred suturing apparatus including a securing mechanism.
Figure 14:
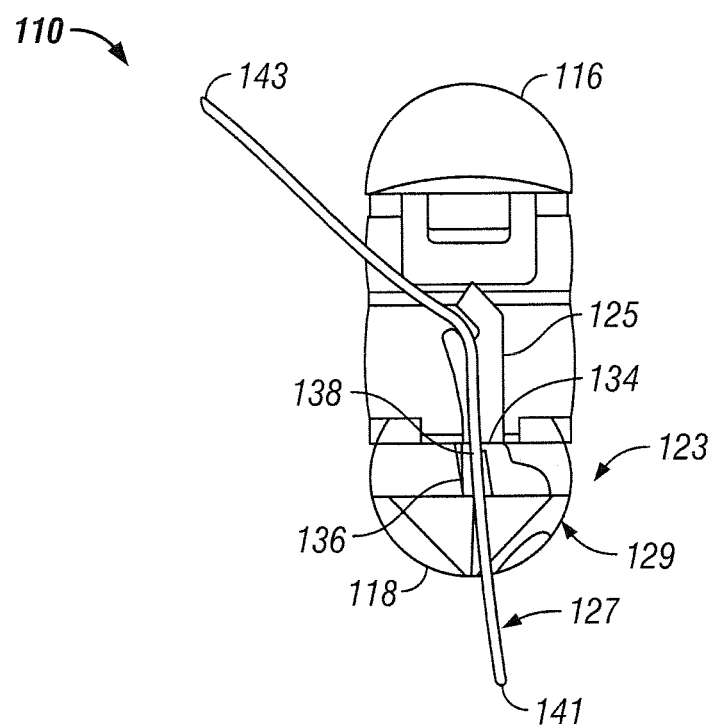
FIG. 14 is a front end view of the fifth suturing apparatus.
Figure 15:
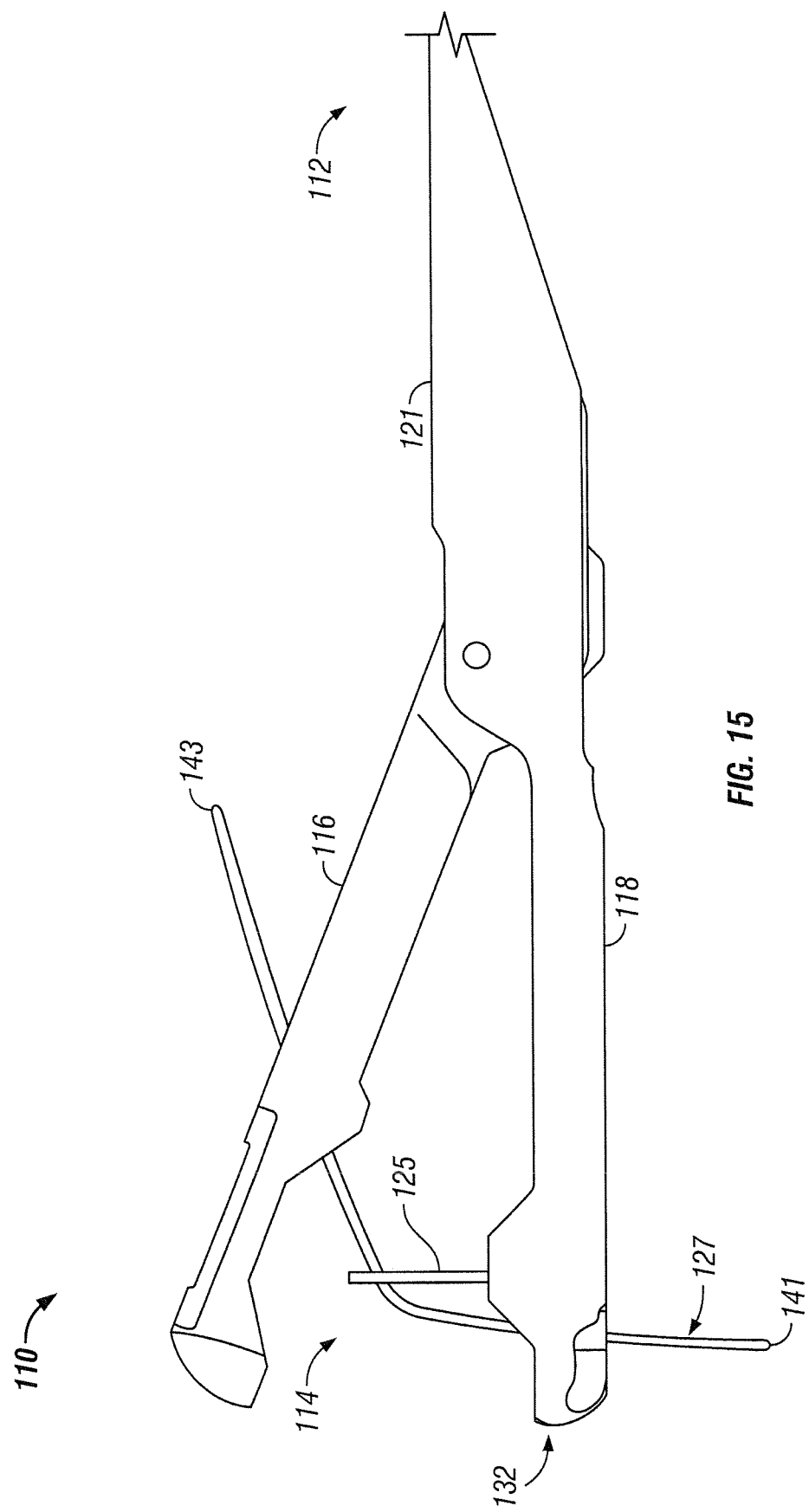
FIG. 15 is a side elevation view of the fifth suturing apparatus.

A fifth preferred embodiment of a suturing apparatus is illustrated in FIG. 13 and designated generally by the reference numeral 110. In FIGS. 13-15, the apparatus 110 includes an elongate configuration with a proximal end 112 and a distal end 114. A handle assembly (not shown) is disposed at the proximal end 112 and may include scissor handles which are operatively coupled to a pair of opposing suturing jaws 116 and 118 at the distal end 114. An elongate shaft or tube 121 couples the jaws 116, 118 to the handle assembly. In one embodiment, the upper jaw 116 is pivotal with respect to the lower jaw 118 as illustrated in FIG. 13-15.

In the illustrated embodiment, the lower jaw 118 includes a retaining mechanism 123 of particular interest to the present invention. The apparatus 110 may include a handle assembly, a bendable needle 125 housed in one of the jaws 116,118, and a suture receiver included in the other of the jaws 116,118 as described above. Since the retaining mechanism 123 serves to securely hold a suture 127 while easily permitting its release when engaged by the needle 125, the mechanism 123 is preferably included in the jaw that houses the needle 125. For example, if the needle 125 is housed in the upper jaw 116, then the retaining mechanism 123 would also be included in the upper jaw 116.

Figure 16:
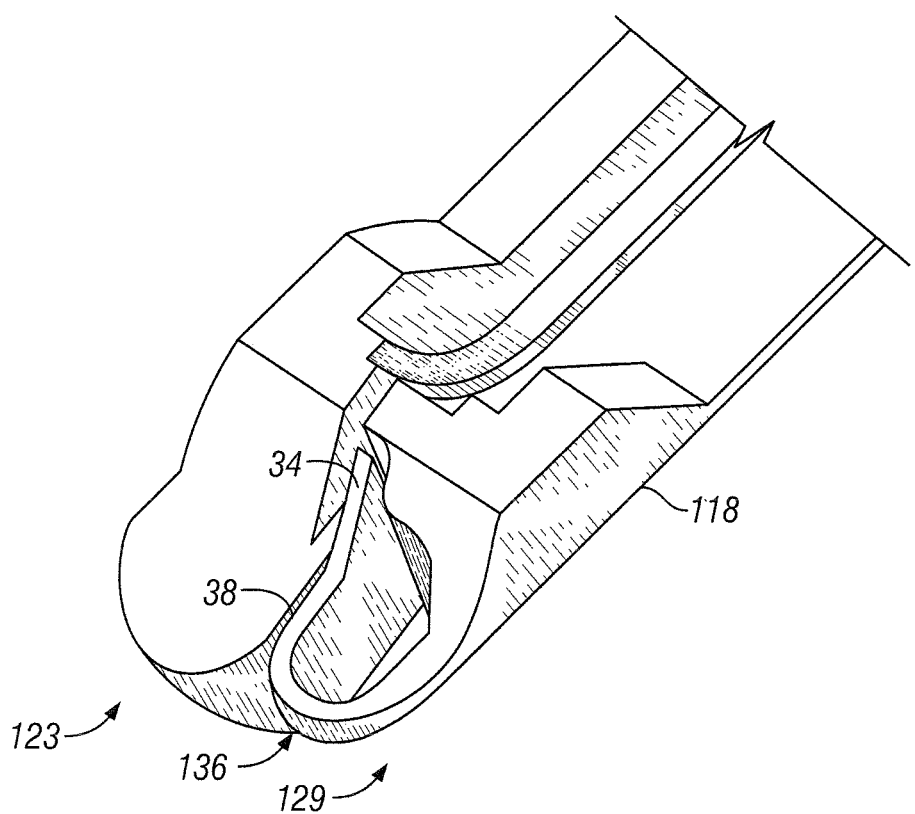
FIG. 16 is a close-up, perspective view of a suturing jaw incorporating the securing mechanism.
Figure 17:
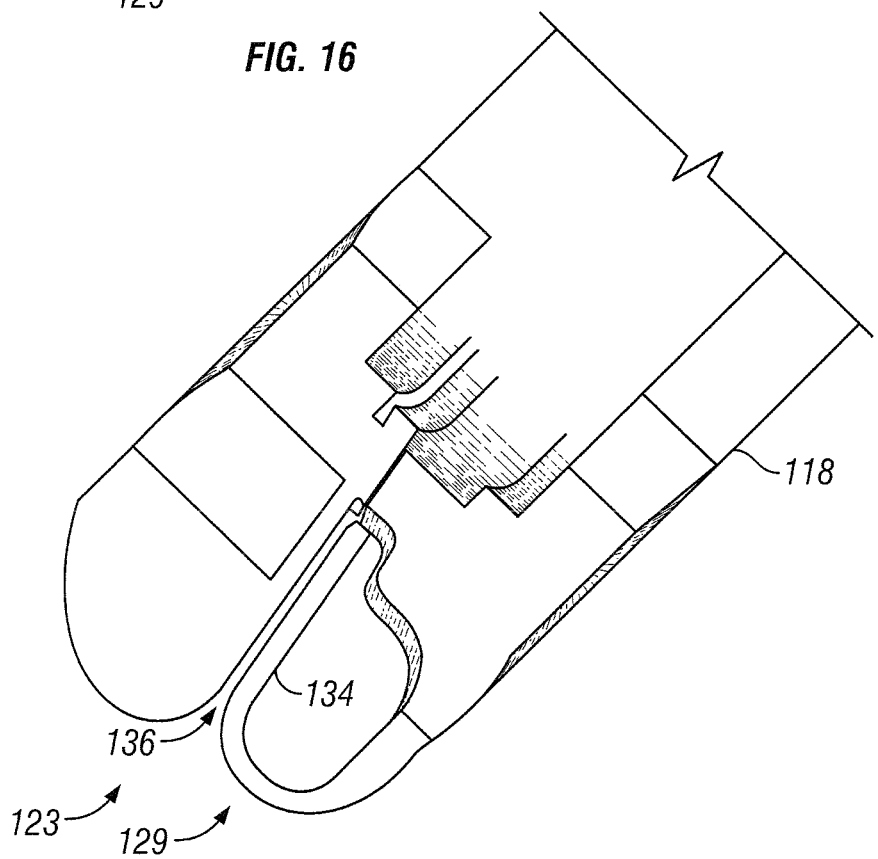
FIG. 17 is a top plan view of a tip of the suturing jaw of FIG. 16.

A first preferred securing mechanism 123 comprises a spring 129 formed at a distal tip 132 of the jaw 118. The spring 129 includes a cantilever portion 134 bent back on itself. A wedge, or groove, 136 is defined between the cantilever portion 134 and an opposite wall 138 as shown more clearly in FIGS. 16 and 17. In the illustrated embodiment of FIGS. 13-16, the securing mechanism 123 is formed integrally with the jaw 118. To assemble the suture 127, a first end 141 is held beneath the jaw 118 and the other end 143 above the jaw 118. The ends 141, 143 may be pulled in a proximal direction such that the suture 127 is wedged into the groove 136. When disposed in the groove 136, the cantilever portion 134 biases the suture 127 against the opposite wall 138, thus pinching the suture 127 securely in place for engagement by the needle 125.

The biasing force of the spring 129 is configured such that the suture 127 is both held securely absent engagement by the needle 125, and yet is permitted to be easily released upon engagement. It is to be expressly understood, therefore, that the spring 129 may comprise a variety of mechanisms capable of abutting, or pinching, the suture 127 against an opposing surface while permitting its release upon engagement with a needle. The groove 136 is preferably aligned with or disposed adjacent to a needle exit port 145 such that when the ends 141, 143 are tugged proximally, a portion 147 of the suture 127 lies along the path of the transversely extending needle 125.

Figure 18:
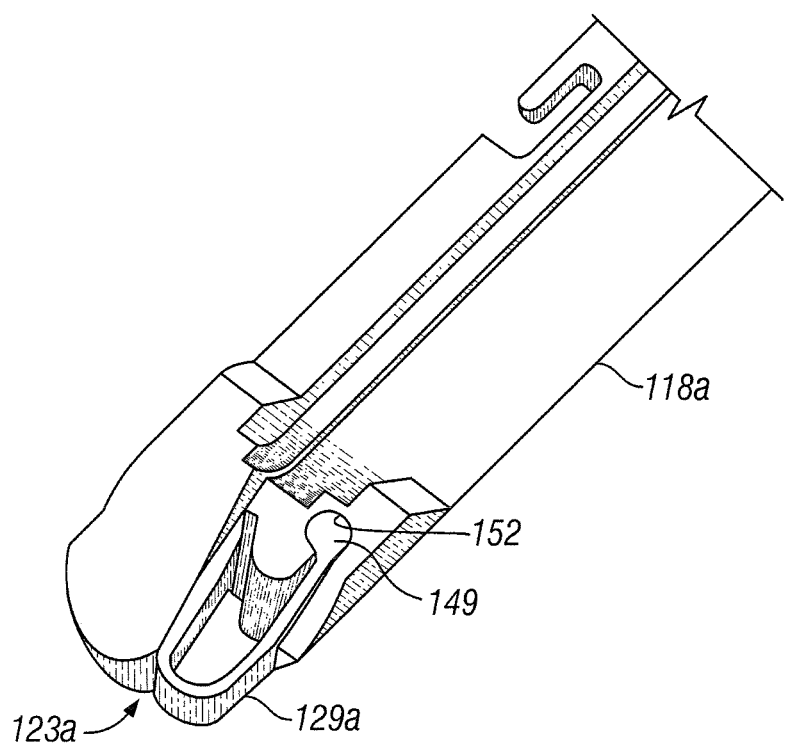
FIG. 18 is a perspective view of a suturing jaw incorporating an alternative securing mechanism.

In FIG. 18, a second preferred retaining mechanism 123*a* may include a spring mechanism 129*a* formed separately from the jaw 118*a*. The spring mechanism 129*a* includes an anchor 149 configured to fit within a slot 152 defined in the jaw 118*a*.

Figure 19:
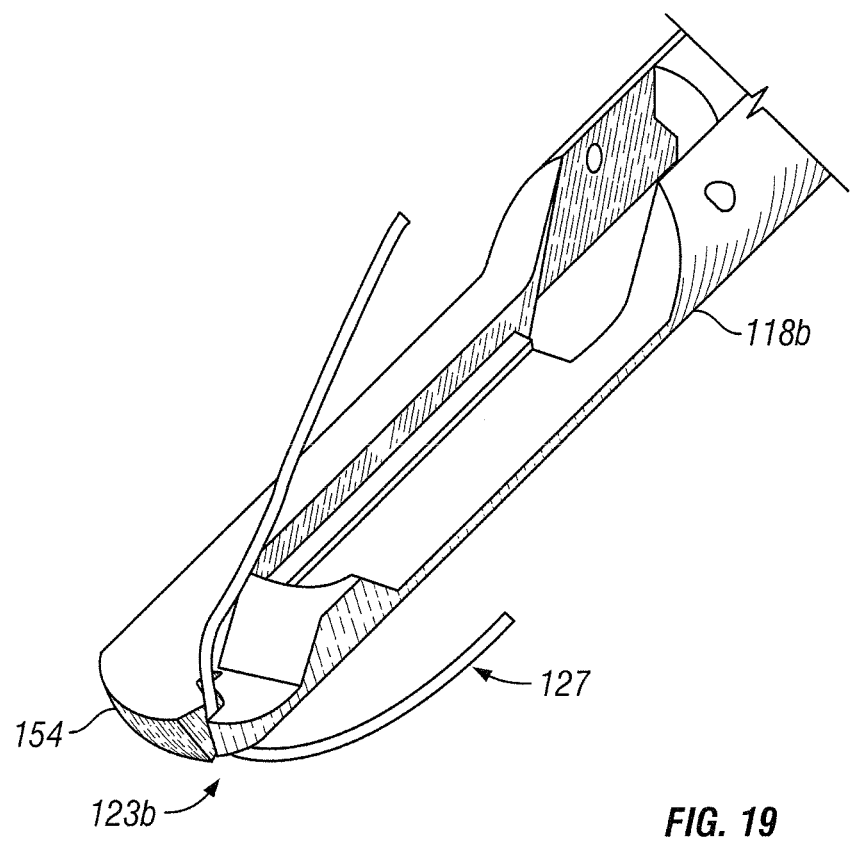
FIG. 19 is a close-up perspective of a suturing jaw incorporating a further alternative securing mechanism.
Figure 20:
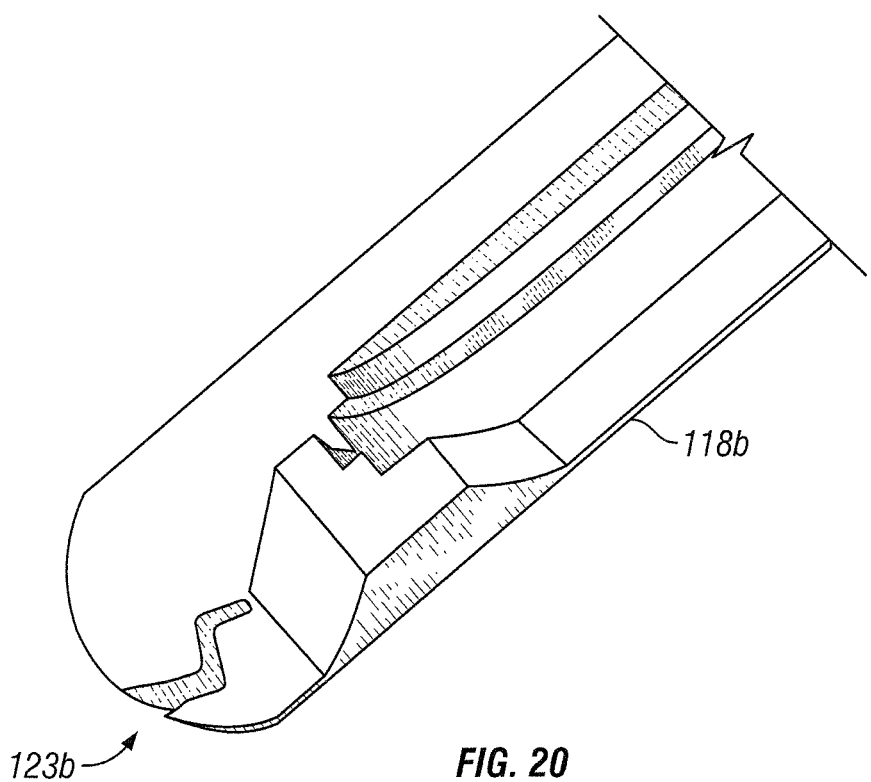
FIG. 20 is a perspective view of the suturing jaw of FIG. 19.

In FIGS. 19 and 20, a third preferred retaining mechanism 123*b* comprises a zigzag groove 154 that becomes increasingly narrow as it extends proximally. The zigzag pattern in combination with the proximal tapering facilitates a tight fit when the suture 127 is drawn proximally. In particular, the proximally tapered configuration of the groove 154 pinches the suture in place as it drawn proximally while the zigzag pattern prevents the suture 127 from being distally disengaged from the jaw 118*b*.

Figure 21:
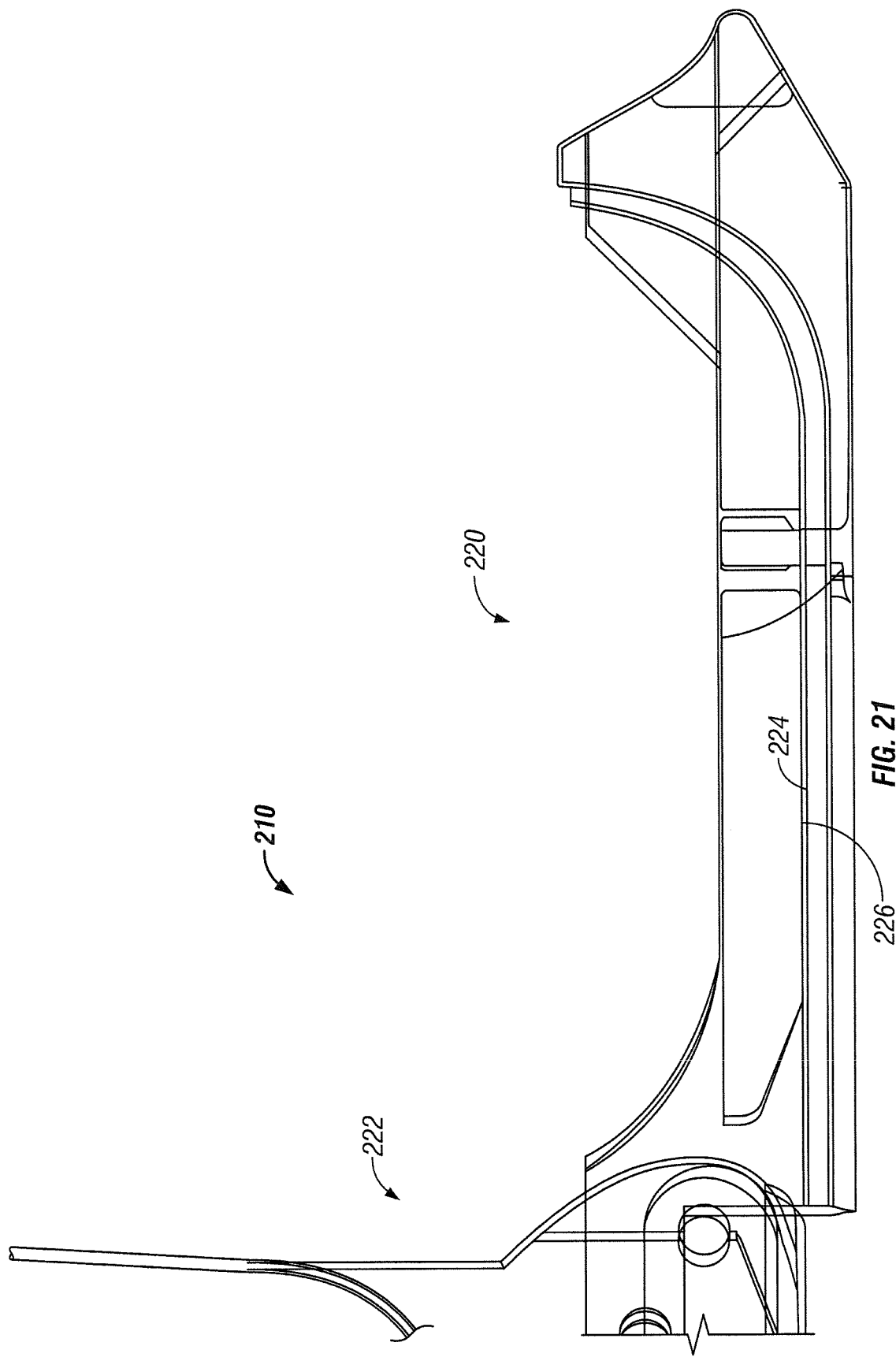
FIG. 21 is a partially removed side elevation view of a sixth preferred suturing apparatus.
Figure 22:
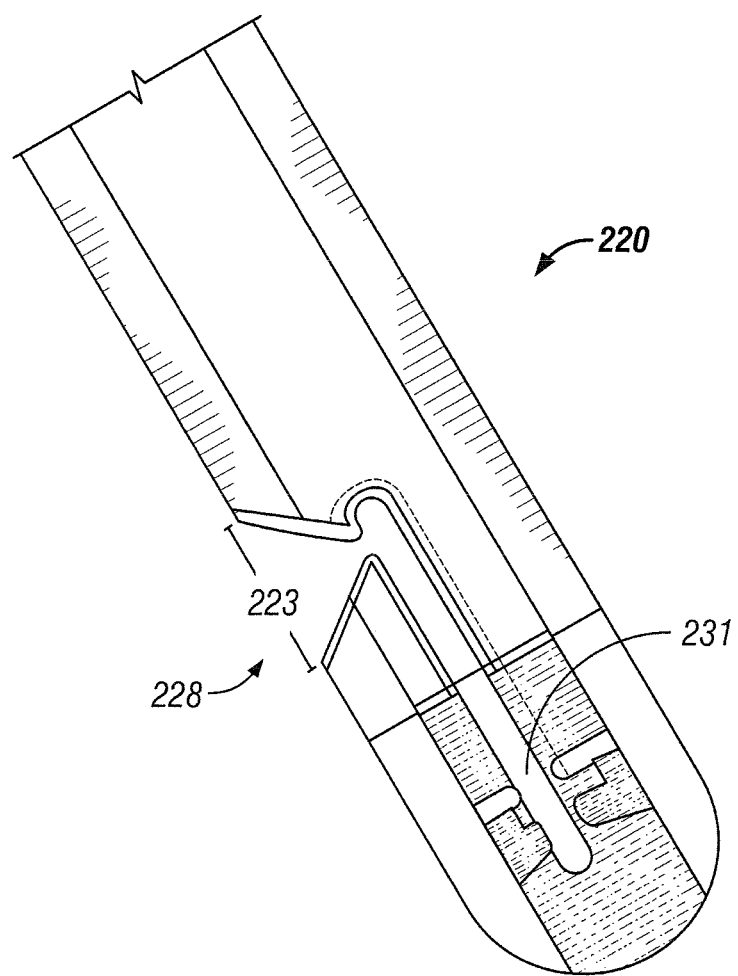
FIG. 22 is a top plan view of a needle carrying jaw of the sixth preferred suturing apparatus.
Figure 23:
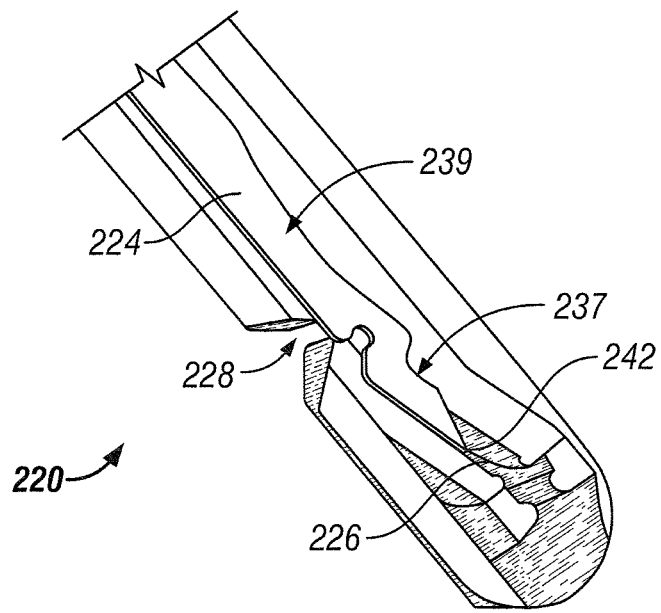
FIG. 23 is a perspective view of the needle carrying jaw of FIG. 22 with a bendable needle shown overlaid for clarity.

A sixth embodiment of a suturing apparatus is shown in FIGS. 21-27 and designated generally by the reference numeral 210. The apparatus 210 comprises a first jaw 220 and a second jaw 222 that are pivotal with respect to each other. In FIGS. 21-23, the first jaw 220 is configured to house a bendable needle 224. This needle carrying jaw 220 may comprise either the lower or upper jaw of the apparatus 210. The bendable needle 224 is substantially disposed in a channel 226 within the first jaw 220 when the needle 224 is in a non-operative, or non-piercing, position.

In FIG. 22, the first jaw 220 defines an opening, or ingress 228, that is in communication with an axial slot 231. The ingress 228 is preferably provided with a relatively wide mouth 233 is open to one of the sides of the first jaw 220. This preferably lateral ingress 228 tapers as it approaches the axial slot 231.

In FIG. 23, the needle 224 of particular interest to the invention is shown out of position, overlaying the first jaw 220 for clarity. When assembled, the needle 224 would reside in the channel 226 as discussed above. The needle 224 comprises a lateral slot, or notch 235 (see FIG. 28). An edge defining the notch 235 is preferably radiused, or smoothed, such it would not cut a suture. As best shown in original FIG. 28, the needle 224 comprises distal portions that define a sharp needle tip 242, notch or slot portions that define the notch or slot 235 and its associated opening, and first and second void portions that define a first distal crescent-shaped void 237 and an adjacent second proximal crescent-shaped void 239. In the preferred needle of original FIG. 28, the distal portions that define the sharp needle tip 242 are equally bifurcated by the needle's axis. As further shown in FIG. 28, the slot portions defining the slot 235 define a base and a channel extending laterally of the base, the preferred base being configured as a circle with a diameter that is greater than a width of the channel. The voids 237, 239 collectively provide flexibility that is spread out on either side of the notch 235, over a greater length of the needle 224, such that all stresses do not collect at the notch 235 when the needle 224 is bent. The notch 235 is preferably disposed between the voids 237, 239. As further shown in original FIG. 28, the first void 237 is shaped like a crescent with a first radius and a first axial length and the second void 239 is shaped like a crescent with a second radius greater than the first radius and with a second axial length greater than the first axial length.

Figure 24:
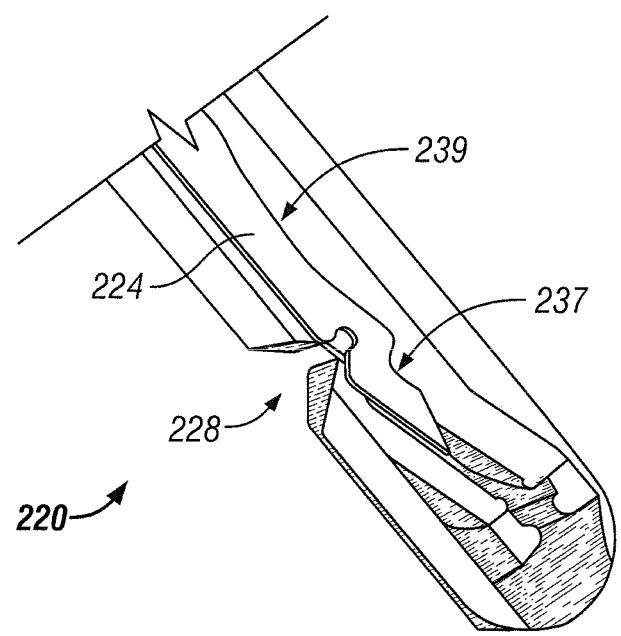
FIG. 24 is a perspective view of the needle carrying jaw with the bendable needle shown overlaid in an aligned position.
Figure 25:
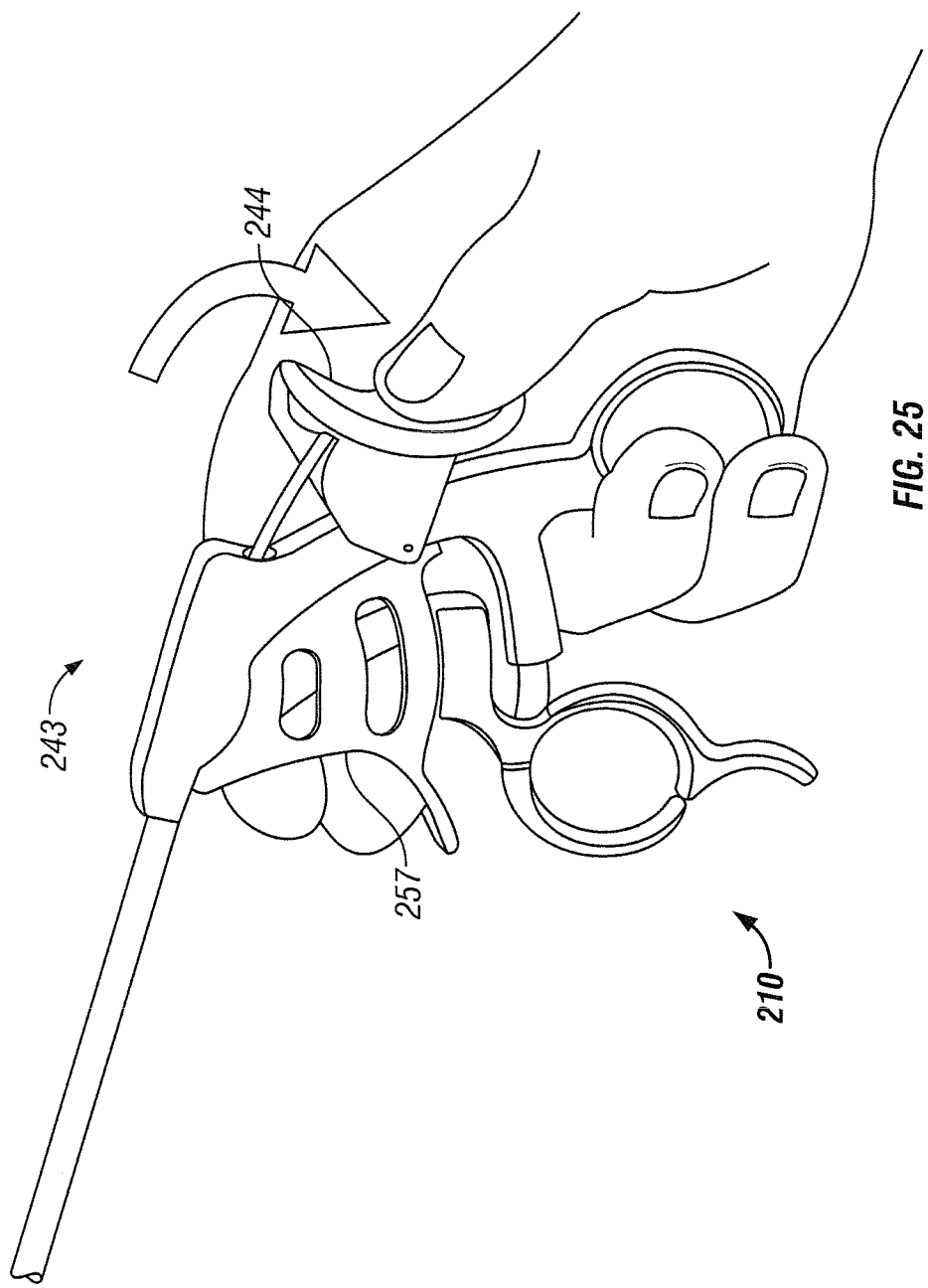
FIG. 25 is a perspective view of a handle assembly for the sixth preferred suturing apparatus including a preferred needle actuator.

In a rest state, as shown in original FIG. 23, the needle 224 is generally straight and may be biased to any rest position with respect to the ingress 228. For example, the rest position may comprise the notch 235 being disposed distally to the ingress 228, as shown in FIG. 23, or proximally to the ingress 228. To load a suture, the needle 224 is moved to a loading position whereby the notch 235 is aligned with the ingress 228 as shown in FIG. 24. If the needle 224 is biased such that the notch 235 is distal to the ingress 228, alignment is reached by moving the needle 224 in a proximal direction with respect to the first jaw 220. Accordingly, if the needle 224 were biased such that the notch 235 is proximal to the ingress 228, alignment is reached by moving the needle 224 in a distal direction with respect to the first jaw 220. FIG. 25 illustrates a preferred handle assembly 243 of the suturing apparatus 210. In FIG. 25, a manually operable actuator 244 is coupled to the needle to enable movement, proximally and distally, thereof. In the illustrated embodiment, the actuator 244 preferably comprises a thumb lever, or rocker, that may be cocked backward by a user's thumb, thereby moving the needle proximally to align the notch with the ingress, and moved forward, thereby advancing the needle distally.

Figure 26:
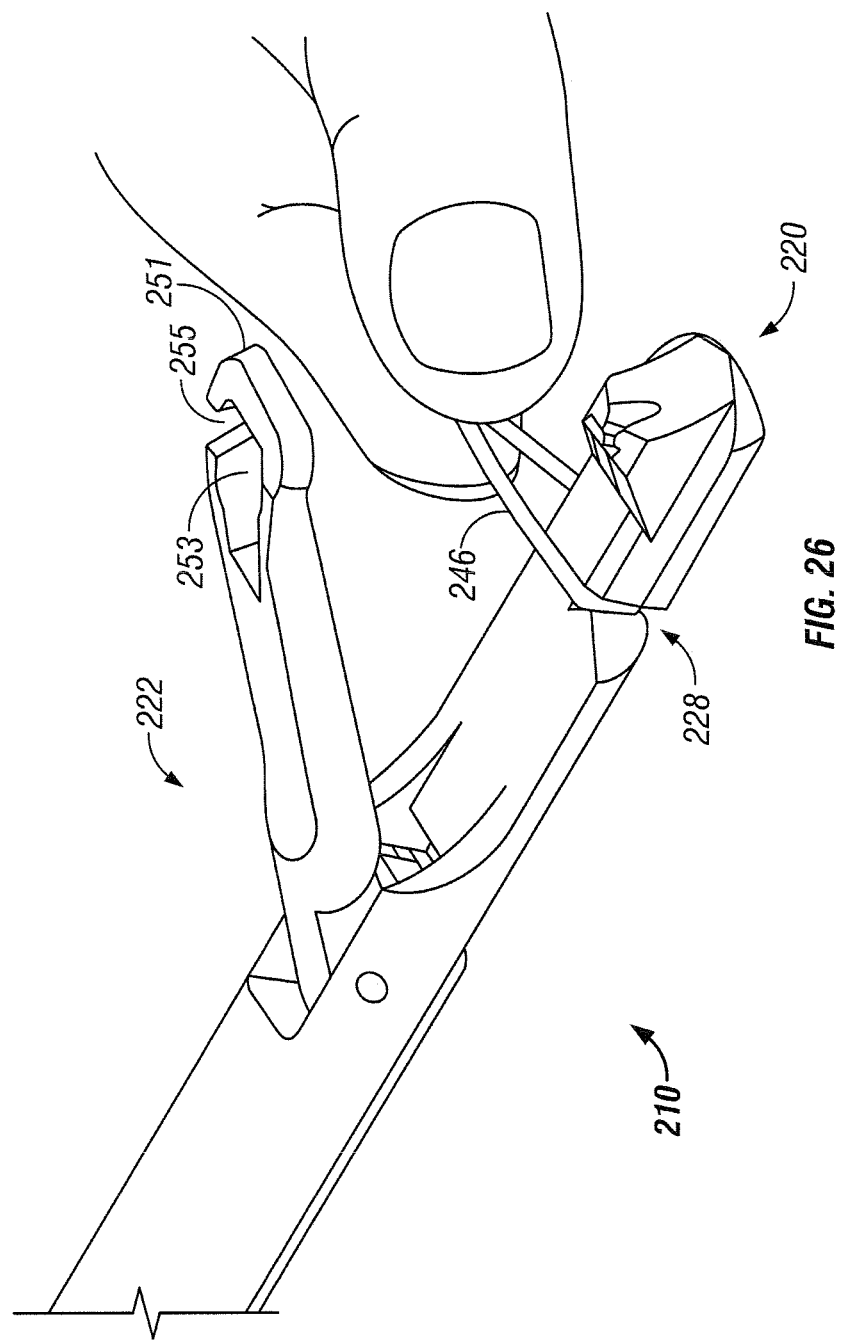
FIG. 26 is a perspective view of the sixth preferred suturing apparatus being loaded with a suture.

FIG. 26 illustrates a suture 246 being loaded onto the apparatus 210. The suture 246 is formed into a loop and threaded into the ingress 228. With the suture 246 held slightly taut across the first jaw 220, the suture 246 has entered the ingress 228 and is now disposed in the notch of the needle. The finger slide, shown in FIG. 25, may now be released, thereby distally biasing the needle with the captured suture 246 to the resting position as shown in FIG. 27.

It will be appreciated that the axial slot 231 of the first jaw 220 allows the captured suture 246 to travel freely as it is carried by the needle 224.

A transition block 248 is provided at a distal portion of the first jaw 220 and may be integral with or separate from the jaw 220. The transition block 248 may be adapted to curve the needle and direct it at any desired angle, shown in the illustrated embodiment as generally perpendicular to the axis of the first jaw 220.

Figure 27:
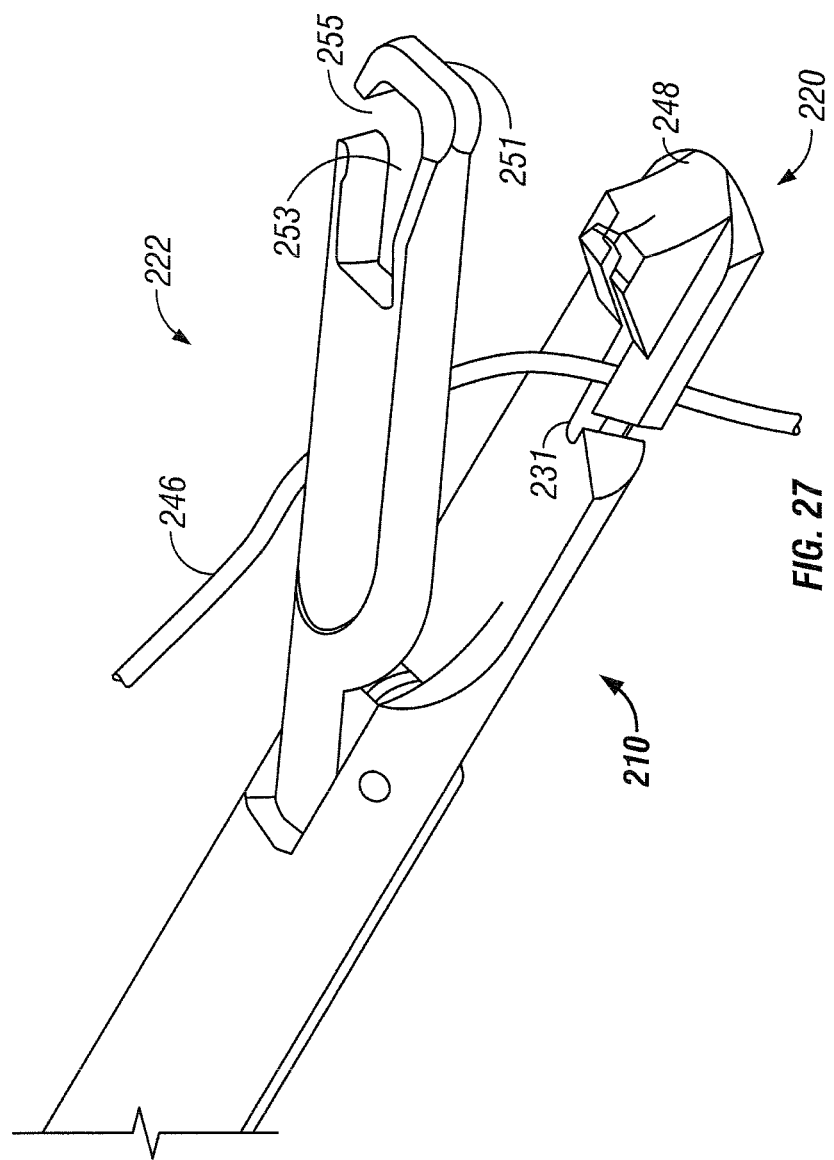
FIG. 27 is perspective view of the sixth preferred suturing apparatus with the suture loaded.

In FIGS. 26 and 27, the second jaw 222 comprises a distal hook 251 that defines an aperture 253 with a side opening 255. When the jaws 220, 222 are clamped on a piece of tissue, the aperture 253 is configured to enable the needle to pass through after piercing the tissue. As the needle 224 is retracted the tissue acts as a suture receiver by holding on to the suture 246 while the needle 224 is withdrawn. This leaves a loop or free line of suture 246 on the side of the tissue in contact with the jaw 222. The hook 251 can then be placed in the loop and pulled. Alternatively, the two jaws 220, 222 can be grasped on the free line of suture and pulled through the tissue. In FIG. 25, a stationary finger support 257 serves as a counterforce plate for the actuator 244.

Figure 28:
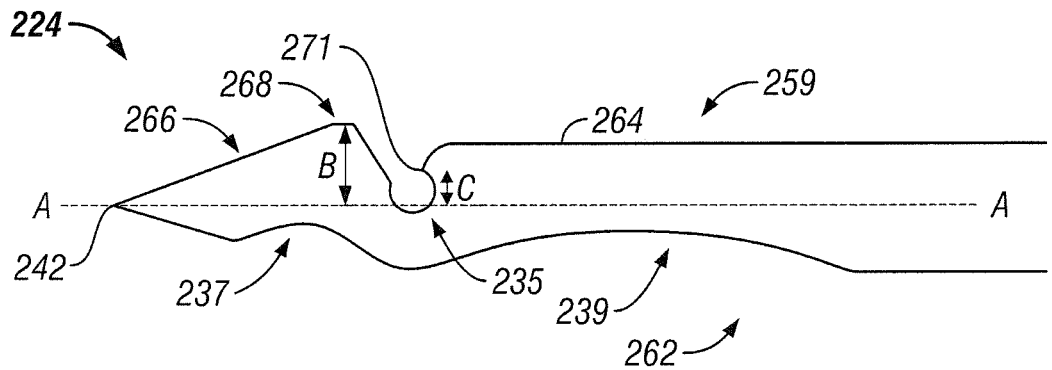
FIG. 28 is an elevation view of a preferred bendable needle according to the invention.

In FIG. 28, the preferred bendable needle 224 comprises a distal geometry that facilitates a smooth piercing of tissue by preventing the tissue from being snagged or caught by any part of the needle 224. The needle 224 comprises a notch side 259 and an opposite, void side 262. In particular, the needle 224 comprises a straight, notch-side edge 264 located proximally to a notch edge defining the notch 235. The needle 224 also defines a needle axis "A" that extends generally parallel to the notch-side edge 264.

As the needle 224 pierces a tissue, the tissue will travel along a notch-side ramp 266 that leads to a distal ledge 268 disposed distally of the notch edge defining the notch 235. As shown, a distal notch edge extends from the base and laterally from the axis for a first distance and a proximal notch edge that extends laterally from the base and laterally from the axis for a second distance that is less than the first distance. It will be appreciated that the distal ledge 268 is spaced a transverse distance "B" from the axis "A" while a proximal ledge 271 is spaced a transverse distance "C" from the axis "A." In the preferred embodiment, distance "B" is greater than distance "C" such that the distal ledge 268 pushes the pierced tissue outward to help keep the tissue from getting caught in the notch 235. As the tissue travels over the notch 235, a generally rounded bump that is associated with the proximal ledge 271 further prevents the tissue from getting snagged.

On the opposite, void side 262, first and second void edges define the first and second voids 237, 239 that distribute the stresses more evenly across the needle 224 and around the notch 235 when the needle 224 is bent, such that the stresses are minimized near the notch 235. The opening to the notch 235 is directed distally such that the suture is forced into the needle during deployment through the tissue and so that the suture releases easily as the needle is retracted.

Figure 29:
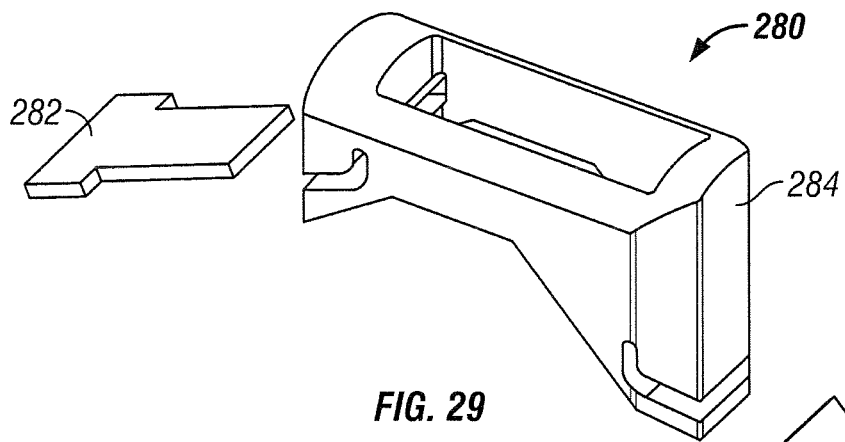
FIG. 29 is a partially exploded, perspective view of a preferred suture receiving mechanism.
Figure 30:
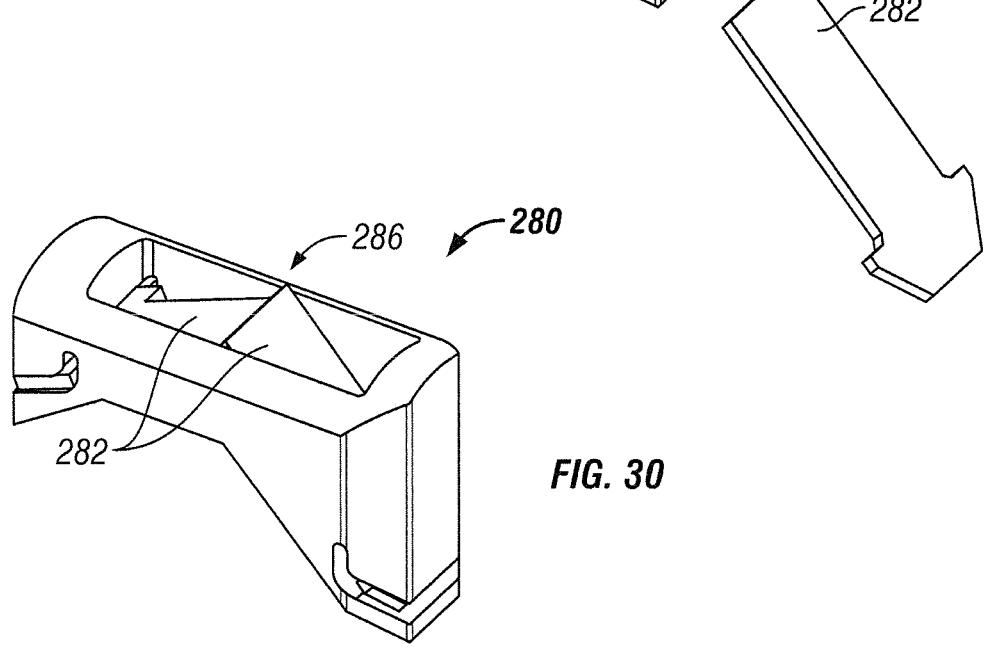
FIG. 30 is a perspective view of the preferred suture receiving mechanism of FIG. 29.

A further preferred embodiment of a suture receiver 280 is illustrated in FIGS. 29 and 30. The receiver 280 may, for example, be carried by a jaw opposite to the jaw housing a needle. The suture receiver 280 comprises a pair of flaps, or paddles, 282 disposed in a receiver housing 284. The paddles 282 are preferably configured to abut one another at a pinch point 286, as shown in FIG. 30, to permit a needle to travel therebetween while retaining a carried suture when the needle is retracted. As discussed above, employment of a suture receiver is optional as the pierced tissue itself may often time serve as a suture receiver. In particular, after a needle carrying a suture has pierced the piece of tissue, the pierced tissue often times sufficiently retains the suture in the form of a loop as the needle is retracted.

Figure 31:
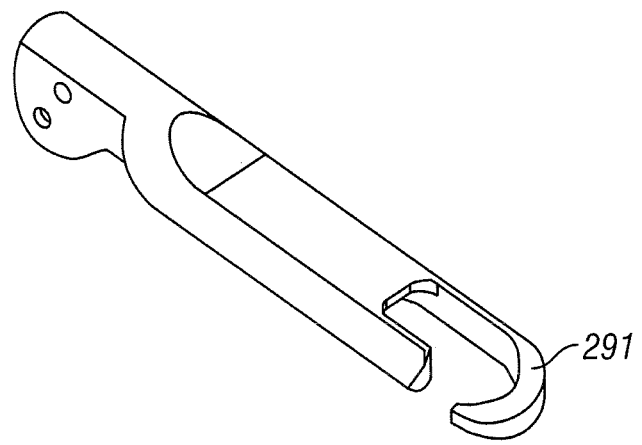
FIG. 31 is a perspective view of a jaw comprising a single barb.
Figure 32:
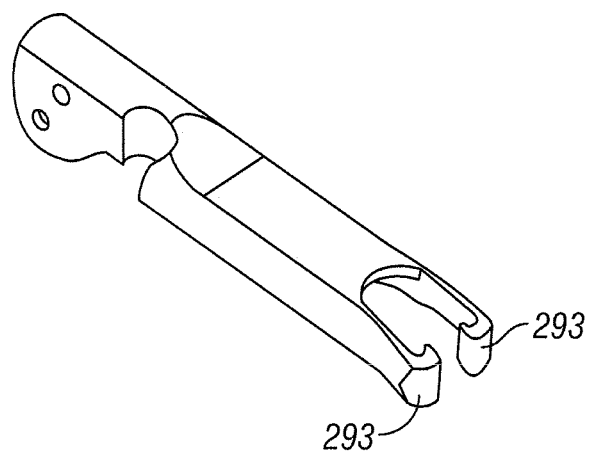
FIG. 32 is a perspective view of a jaw comprising a pair of barbs.

In FIG. 31, a first preferred embodiment of a hook, or barb 291, is formed at the distal end of a jaw, preferably the second jaw opposite to the first jaw housing the bendable needle. The barb 291 is configured to hook a looped suture that is retained, for example, by the tissue itself after the bendable has been retracted. In FIG. 32, a distal end of a jaw may alternatively be formed with a pair of barbs 293.

The above-described embodiments generally represent a significant advance in the suture passing art because they permit suture to be retained in a device for delivery to a surgical site and in particular via an arthroscopic cannula, permit the tissue to be grasped and re-grasped if necessary, and permit the suture to be pushed through the tissue with a reciprocating bendable needle. However, improvements are still possible in terms of how the suture is loaded into the passer for capture by the needle, the construction of the needle, and the overall simplification of needle deployment.

FIGS. 33-48 relate to a new, seventh, and presently preferred embodiment that adds a number of significant advancements.

Figure 33:
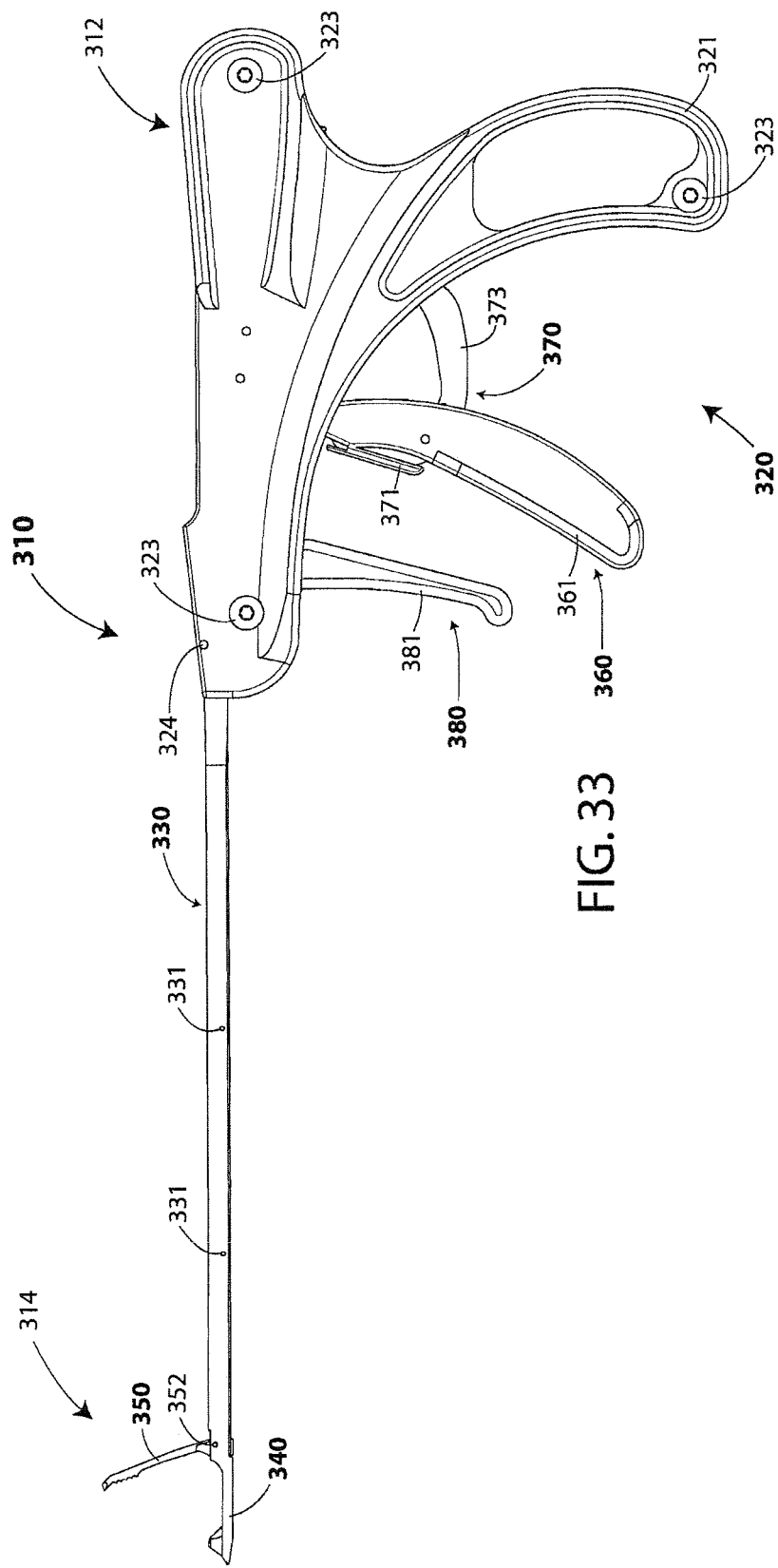
FIG. 33 is a left side view of a suture passing apparatus according to a seventh and presently preferred embodiment.

FIG. 33 is a side view of a novel suture passing apparatus 310 and FIGS. 34-36 show an improved bendable needle 400 for use with the suture passing apparatus 310. As shown in FIG. 33, the suture passing apparatus 310 generally comprises a handle assembly 320 located at a proximal end 312, an elongate shaft 330 extending from the handle assembly 320, and a grasping mechanism formed by a pair of jaws 340, 350 supported at a distal end 314 of the elongate shaft 330 and a jaw movement mechanism 360 and related ratchet latch assembly 370 (described more fully below). The preferred handle assembly 320 is formed from two halves, a left half 321 and a right half 322 (not shown) held together by a plurality of screws 323, and the elongate shaft 330 is held between the two halves with a handle-to-shaft pin 324 that engages a notch (not shown) at a proximal end of the shaft 330. The jaws include a fixed jaw 340 and a moveable jaw 350. The moveable jaw 350, as shown, is pivotally secured to a distal end of the shaft with a jaw-to-shaft pin 352.

As further shown in FIG. 33, and described more fully below, the novel suture passing apparatus 310 includes two mechanisms, a jaw movement mechanism 360 (and related ratchet latch assembly 370) for opening and closing the jaw assembly, and a needle movement mechanism 380 for translating the needle back and forth.

The jaw movement mechanism 360 opens and closes the moveable jaw 350 and is manipulated by way of a jaw trigger 361. The prior embodiments required the surgeon to proactively move the jaw in both the open and closed directions. For simplified use in this embodiment, the moveable jaw 350 is optionally biased open and then moved toward the closed position relative to the fixed jaw 340 when the surgeon squeezes the jaw trigger 361. In addition, the jaw movement mechanism 360 may optionally include a superelastic element that deforms under load to limit jaw closing force.

As already noted, the ratchet latch assembly 370 relates to the jaw movement mechanism 360. The preferred ratchet latch assembly 370 is transparent in its operational nature in that it locks without positive action by the user, but can be disabled with simple depression of a release button, and all without the operator having to change his hand position. In particular, then the jaw trigger 361 is pulled, a moving portion 373 of the ratchet latch assembly 370 travels freely into the handle assembly 320, but through a mechanical interaction more fully described below, prevents the jaw trigger 361 from returning to an open position until later released. For that purpose, the preferred ratchet latch assembly 370 features a ratchet release or finger pad 371 such that the ratchet latch assembly 370 acts like a ratchet when no load is applied to the finger pad 371, while a simple depression of the finger pad 371 releases the ratchet latch assembly 370 and permits the surgeon to vary the position of the jaw trigger 361 and moveable jaw 350 as desired (e.g. for repositioning the jaws as necessary prior to placement of the suture), and if permitted, to return to their open positions.

FIGS. 34-36 illustrate the bendable needle 400 that is intended for use with the suture passing apparatus of FIG. 33. For referential purposes of, the needle 400 has a proximal end 412 and a distal end 414. As shown, the needle 400 is formed from a proximal needle body 401 that has a slotted distal end 402, and a flat bendable extension 403 that within and is welded to the slotted distal end 402 of the needle body 401. The distal end 414 of the bendable needle 400 is similar to the previously preferred needle of FIG. 28 in that it has a needle tip 404, a needle notch 405 on its side, and a notch-side ramp 406 between the tip 404 and the notch 405. However, the presently preferred needle 400 uniquely cooperates with the suture passing apparatus for purposes of loading the suture in a novel way (as described below), and it includes some novel construction features that make it easier to use and safer.

Focusing on the differences that constitute the novel construction for the moment, one can see that the previously disclosed needle body had a right-angle bend at its proximal end that engaged an aperture in a thumb-operated actuator (see e.g. FIG. 25), whereas the needle 400 may include a plastic tab 406 at its proximal end 412 that functions as a proximal loading flag. The preferred plastic tab 406 is made of HDPE, polyethylene, and formed onto the needle body 401 in known manners, but any suitable material and or assembly method may be used.

The plastic tab 406 offers some unique advantages. First, it provides a convenient finger grip for loading the bendable needle 400 into the suture passer 310. In addition, it optionally melts upon autoclaving, thereby enhancing patient safety by effectively preventing reuse of the needle 400.

Figure 37:
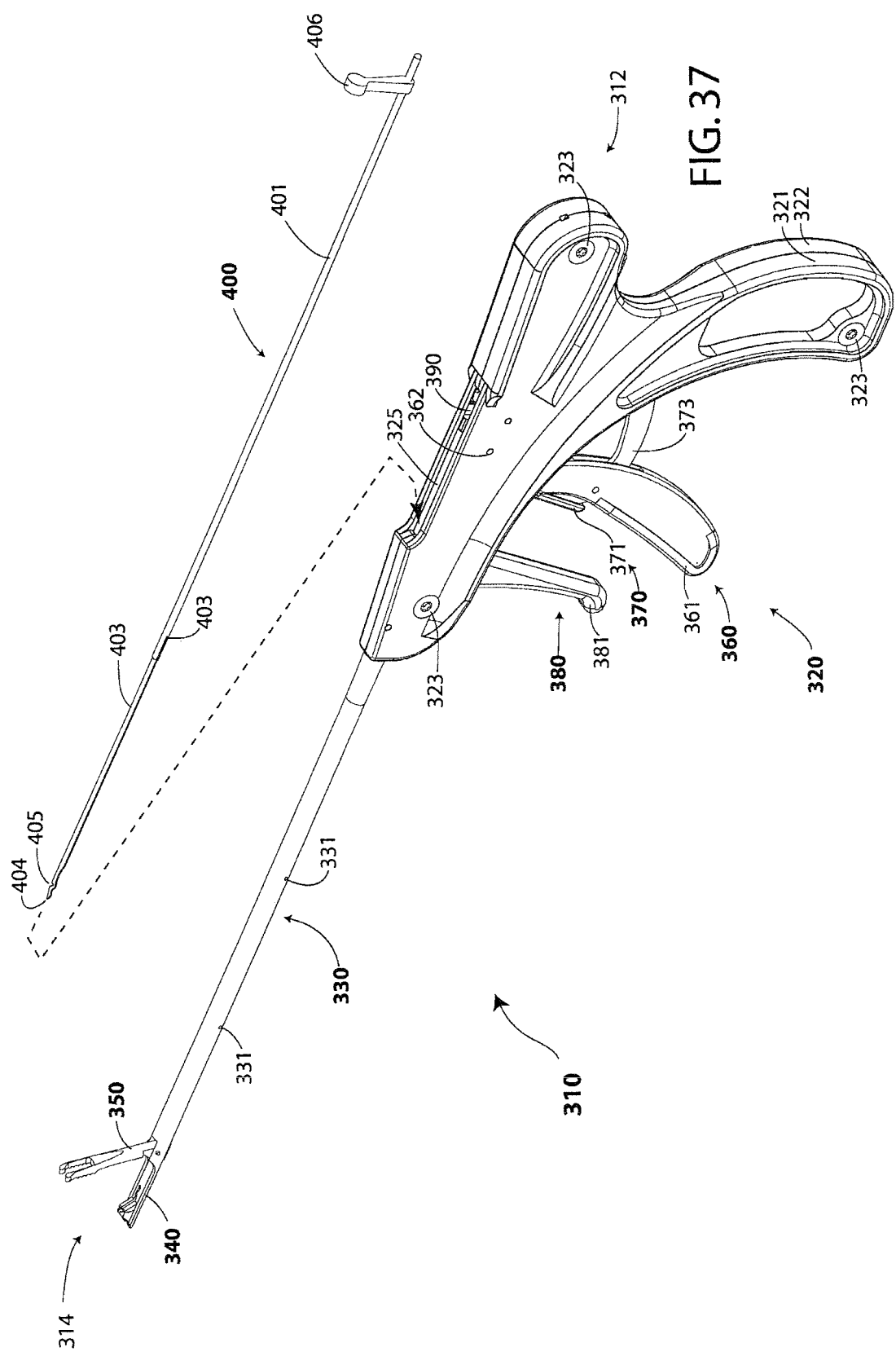
FIG. 37 is a perspective view of the suture passing apparatus of FIG. 33 showing how the bendable needle of FIG. 34 is loaded therein.

FIG. 37 is a partially-exploded perspective view of the preferred suture passing apparatus 310 and the bendable needle 400 that is loaded into the suture passing apparatus. In particular, the dashed line shows how the needle 400 is loaded into the breech or proximal end of the elongate shaft 330 via a chamber 325 located on a top side of the handle assembly 320. As will be more fully described with reference to further figures, after the needle 400 is fully inserted into the elongated shaft 330, the loading flag 406 is pressed down into a needle receiver 390. The needle receiver 390 is moved back and forth by the surgeon's manipulation of the needle trigger 381.

Figure 38:
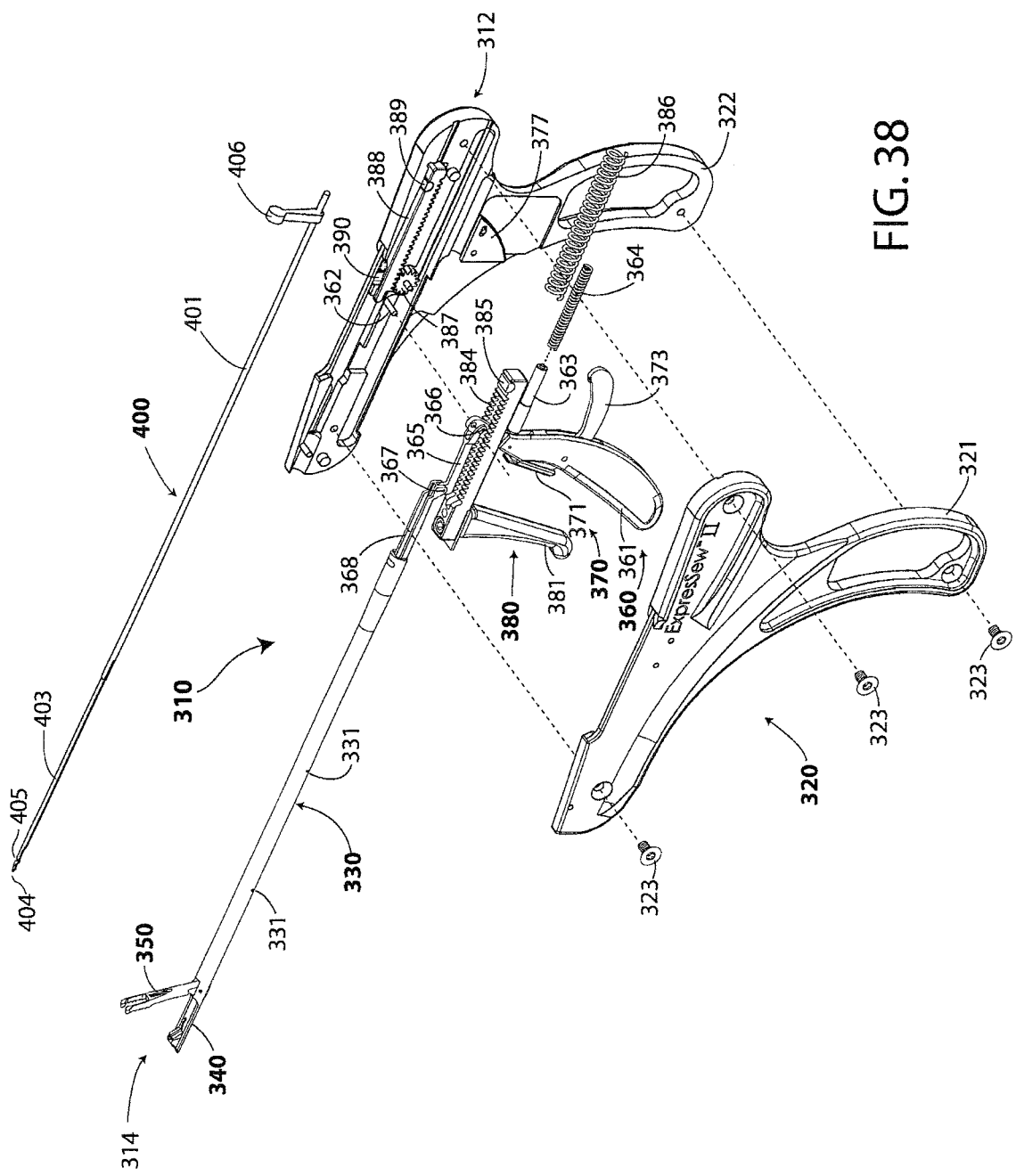
FIG. 38 is an exploded perspective view of the suture passing apparatus of FIG. 33 and the bendable needle of FIG. 34.

FIG. 38 is a fully-exploded perspective view of the preferred suture passing apparatus 310 and the bendable needle 400. Here, one can see the detailed construction of the preferred device, including the components of the jaw movement mechanism 360, ratchet latch assembly 370, and needle movement mechanism 380. For ease of description, the foregoing mechanisms will be described with reference to FIGS. 39-41, which can be reviewed in conjunction with the fully-exploded perspective view of FIG. 38.

Figure 39:
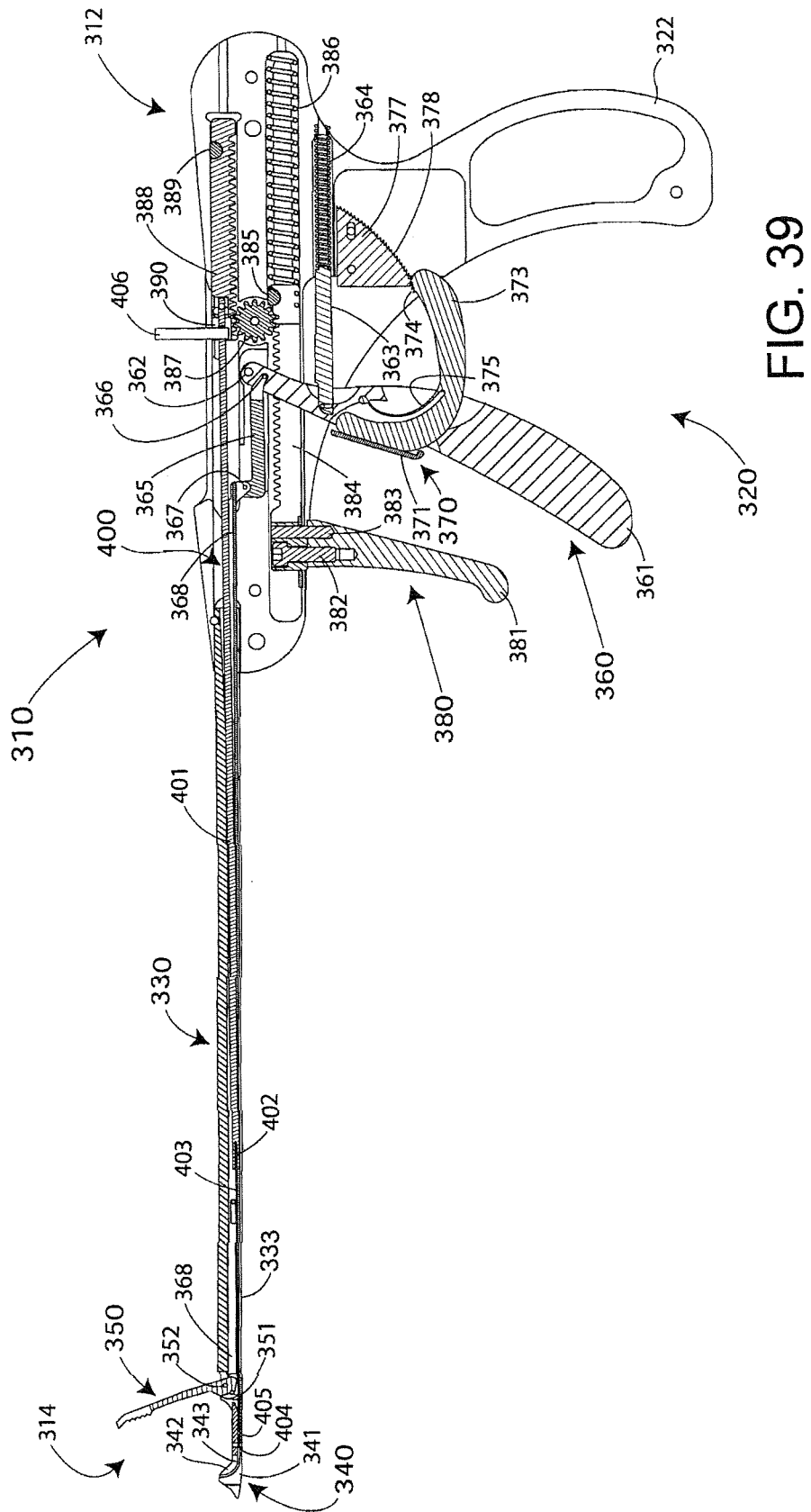
FIG. 39 is a cross-section side view of the suture passing apparatus of FIG. 33 with the bendable needle of FIG. 34 loaded therein.
Figure 40:
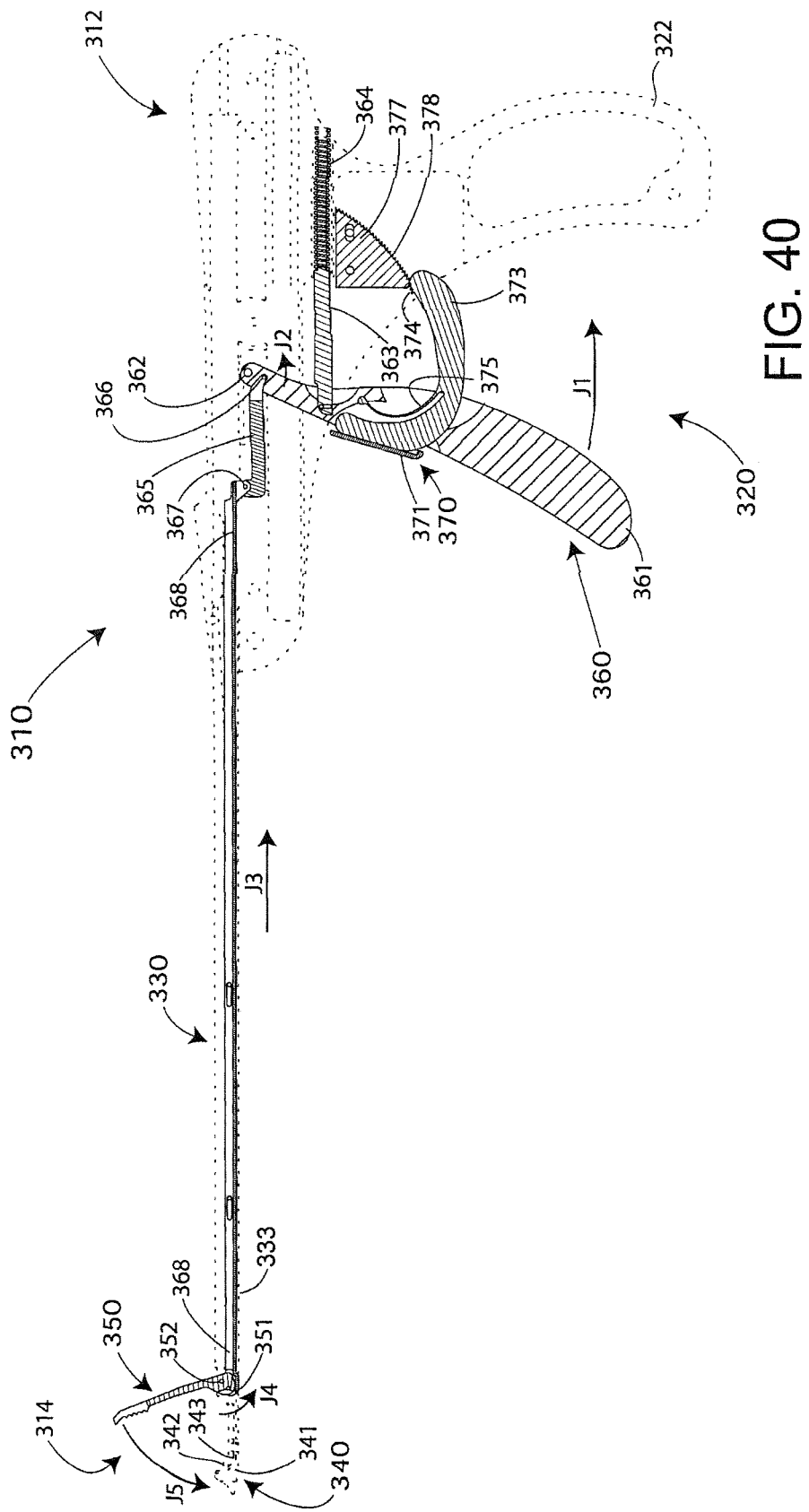
FIG. 40 is a simplified cross-section side view that emphasizes the structure and operation of the jaw movement mechanism.
Figure 41:
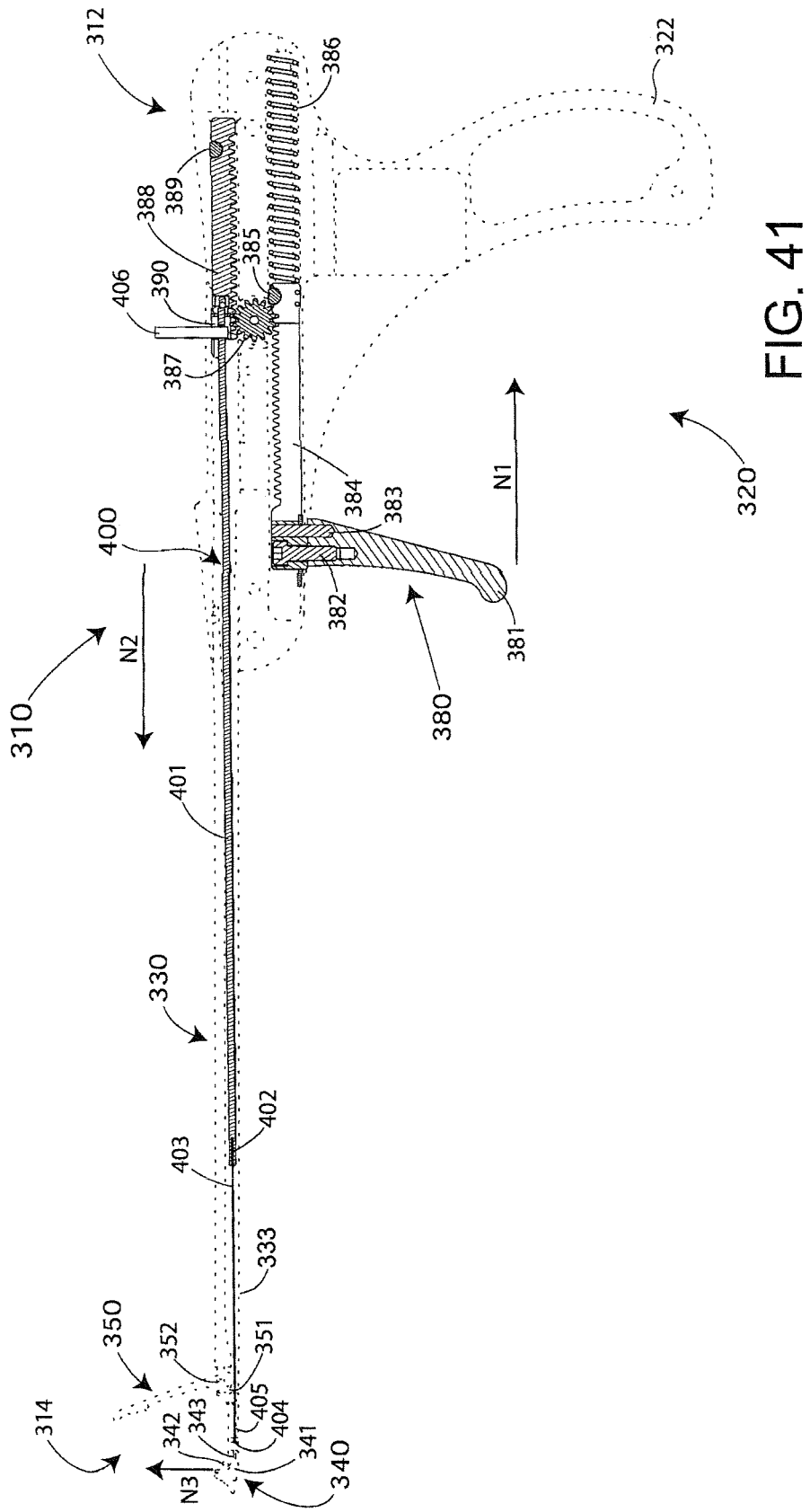
FIG. 41 is a simplified cross-section side view that emphasizes the structure and operation of the needle deployment mechanism.

FIGS. 39-41 are cross-section side views of the suturing apparatus 310 and bendable needle 400 loaded therein. FIG. 39 is a full cross-section, whereas FIGS. 40 and 41 that selectively omit some of the other components, or only shown them in broken line, in order to emphasize the construction and operation of the jaw movement and needle movement mechanisms, 360, 380, respectively.

Figure 42:
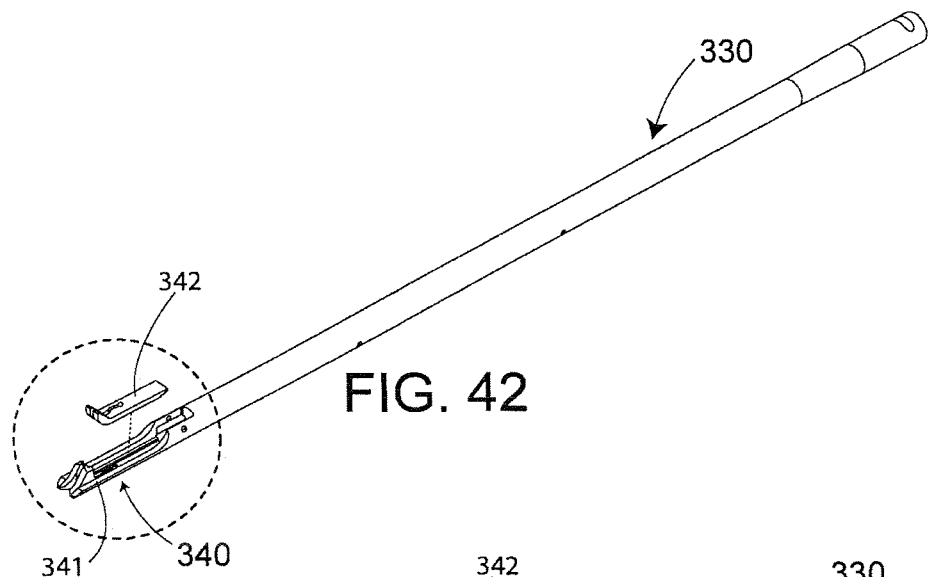
FIG. 42 is an exploded perspective view of the fixed jaw at the distal end of the shaft of suture passing apparatus.
Figure 43:
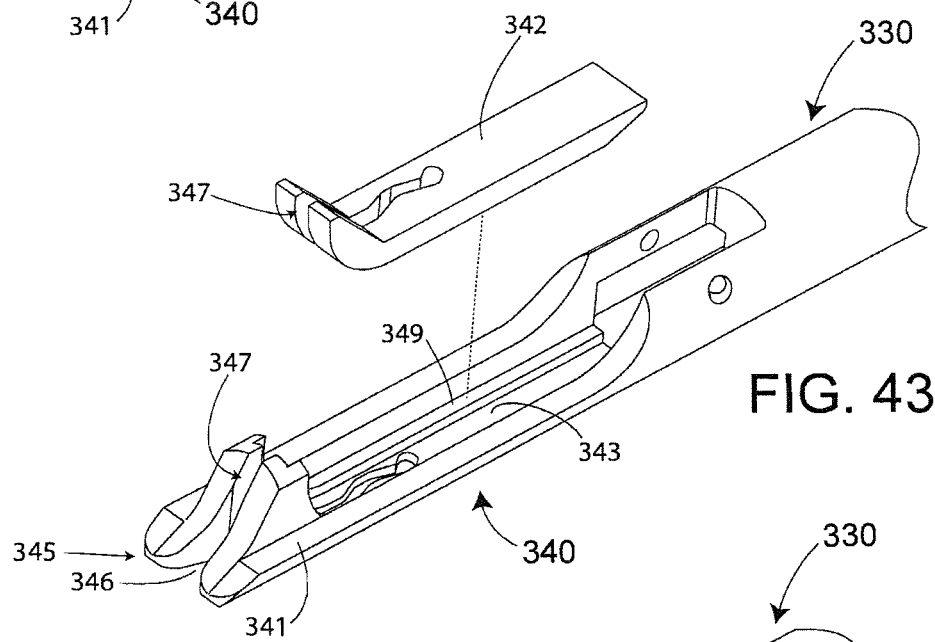
FIG. 43 is an enlarged close-up at the distal tip of FIG. 42.

FIG. 40 focuses on the jaw movement mechanism 360 and related ratchet latch assembly 370 by showing much of the overall apparatus 310 in broken lines and by strategically eliminating the components associated with the needle movement mechanism 380 (see FIG. 42). As shown, the jaw movement mechanism 360 comprises a jaw trigger 361, a jaw trigger pin 362, a jaw trigger push rod 363, a jaw lever spring 364, a link 365, an actuator 368, and, lastly, the moveable jaw 350 itself. In operation, when the jaw trigger 361 is squeezed, it pivots about the jaw trigger pin 362 along arc J1, and the jaw trigger push rod 363 compresses the jaw lever spring 364 which, as noted earlier, tends to bias the jaw trigger 361, moveable jaw 350, and overall jaw motion mechanism 360 in the open position.

As the jaw trigger 361 is moved along arc J1, an upper portion of the jaw trigger 362 is moved through a corresponding, but smaller radius arc J2. In this vicinity, a trigger-to-link pin 366 connects the jaw trigger 361 to the link 365, and further downstream, a link-to-actuator pin 367 connects the link 365 to the actuator 368. Through this series of connections, the arcuate motion of the jaw trigger 361 along arcs J1 and J2 is converted into translational movement of the actuator 368 along arrow J3. As best shown by FIGS. 38, 39 and 40, the elongate shaft 330 is provided with a plurality of guide pins 331, two from each side, and an actuator channel 333 that runs along its length. The actuator 368 slides back and forth within shaft's actuator channel 333.

The actuator 368 is, in turn, connected to a lower portion of the moveable jaw 350 via an actuator-to-jaw pin 351 that is located slightly below the jaw-to-shaft pin 352 about which the moveable jaw 350 rotates. As such, when the jaw trigger 361 is squeezed along arc J1 the upper portion of the trigger 361 is moved along arc J2, the actuator 368 is translated along arrow J3, the proximal end of the moveable jaw 350 is rotated along arc J4, and the distal end of the moveable jaw 350 is rotated along arc J5, i.e. moved toward a closed direction.

FIG. 40 also illustrates the preferred ratchet latch assembly 370 that includes a finger pad 371, a moving portion 373 having sloped teeth 374, and a separate fixed portion 377 that also has sloped teeth 378. The ratchet latch assembly also includes a ratchet latch spring 375 that provides a light spring force to bias sloped teeth 374 of the moving portion 373 against the sloped teeth 378 of the fixed portion 377. The ratchet latch assembly 370 prevents the jaw trigger 361, biased to the opened position by the jaw lever push rod 363 and jaw lever spring 364, from moving to the open position until desired. In particular, the sloping teeth 374 readily slide over the sloping teeth 378 when the jaw trigger is squeezed along arc J1 in a counterclockwise direction to close the moveable jaw 350, but the teeth 374, 378 tend to lock together to prevent the jaw trigger 361 from returning in the clockwise direction and opening the moveable jaw 350. When the surgeon desires to open the moveable jaw 350, he simply depresses the finger pad 371 which rocks the sloped teeth on the moveable portion 373 away from the sloped teeth 378 on the fixed portion 377. At that point, the jaw spring 365 tends to open the jaw movement mechanism 360, as controlled by the surgeon's finger on the finger pad 371. A further beneficial aspect of the novel handle mechanism is a "ratchet on demand" feature. In the preferred embodiment, this feature is provided by the placement of the ratchet button or finger pad 371 on an upper portion of the jaw trigger 361. This enables the surgeon to choose whether or not to use the locking feature by varying how he grips the handle with his fingers—squeezing the jaw trigger 361 without depressing the finger pad 371 permits the ratchet latch assembly 370 to naturally engage, whereas moving the jaw trigger 361 with light but continuous finger pressure on the finger pad 371 enables a repeated opening and closing of the jaw 350 without engaging the ratchet latch assembly 370. In order to permit the surgeon to enable or disable the ratchet latch assembly as desired by varying the pressure applied to the finger pad 371 through the motion of the jaw trigger 361, the spring force of the ratchet latch spring 375 that affects the finger pad 371 is much less than the spring force of the jaw lever spring 364 that affects the overall jaw trigger 361.

FIG. 41 focuses on the needle movement mechanism 380 in the context of the overall apparatus 310 shown in broken lines and, in this case, by strategically eliminating the components associated with the jaw movement mechanism 360 and ratchet latch assembly 370 (see FIG. 41). As shown, the needle movement mechanism 380 comprises a needle trigger 381, a trigger rack 384, a needle spring 386, a gear 387, a needle rack 388 having a needle receiver 390, and lastly, the needle 400. The needle trigger 381 is connected to the needle rack 384, as shown, by a cap screw 382 and a pin 384. Each of the gear racks 384, 388 includes a corresponding rack guide 385, 389, which provides a low surface-area contact surface for ease of movement.

The needle spring 386 biases the needle in the non-deployed or resting state, as shown in FIG. 41. In operation, as the trigger rack 384 is translated toward the proximal end 312 of the device 310 along arrow N1 (to the right), the gear 387 translates the needle rack 388 and needle toward the distal end 314 of the device 310 along arrow N2 (to the left). When the needle 400 is translated toward the distal end 312, it moves through a needle channel 343 in the fixed jaw 340 and ultimately, curves upward, where it temporarily extends from the lower, fixed jaw 340 along arrow N3.

The needle spring 386 must provide sufficient spring force to automatically retract the needle 400 when the needle trigger 381 is released. And, the surgeon must overcome this spring force when he squeezes the needle trigger 381 to deploy the needle 400. It is desirable, therefore, to reduce the required spring force to minimize or even eliminate hand fatigue relating to repeated actuations. For this purpose, the preferred needle 400 is coated with a lubricious coating that makes it easier to slide the needle 400 back and forth in the device 310 and within the patient's tissue. This lubricious coating reduces the needle's coefficient of friction and thereby lowers the spring force needed to retract the needle 400. The use of a lubricious coating makes the suturing device 310 easier to use by reducing the required spring force by about 20%. The preferred coating is a cured polytetrafluoroethylene (PTFE) coating, but any other fluoropolymer or ultra-low sheer solid would suffice. The needle 400 may be coated by simply dipping it into a container of PTFE particles that have been suspended in a suitable solvent (the solvent flashing off after the needle is removed from the suspension and leaving behind the PTFE coating). Preferably, however, the needle 400 is heat cured after being coated in order to melt the PTFE to itself and form a more abrasion resistant coating.

FIGS. 42-48 collectively focus on the unique construction of the suture loading and deployment arrangement as embodied in the novel suturing apparatus' lower jaw 340. As shown throughout FIGS. 42-48, the lower or fixed jaw 340 is located at a distal end of the elongated shaft 330. In this preferred embodiment, the fixed jaw 340 is formed from a lower jaw body 341 that is integrally formed from the same stock as the elongate shaft 330, in combination with a jaw insert 342 that is generally shaped like a ski tip. During assembly, the jaw insert 342 is dropped into and secured to the lower jaw body 341 in any suitable manner, e.g. welding.

The jaw insert 342 helps define a needle channel 343 which guides the needle 400 forward and then up and out during deployment. In particular, as best understood by viewing FIG. 43, and then FIGS. 44 and 48, the jaw insert 342 ultimately rests on and spans a pair of ledges 349 (only one is visible) that surrounds the floor and side walls of the needle channel 343 already formed in the lower jaw body. In essence, the bottom of the jaw insert 342 serves as the ceiling of the needle channel 343. As explained in more detail below, the needle 400 (not shown in FIGS. 42-48) is translated horizontally through the needle channel 343 which includes a curve that directs the needle upward toward and ultimately out of channel exit 344.

FIGS. 42-48 also illustrate a unique construction that relates to the initial loading of the suture (not shown). In particular, the lower jaw 340 has a forked distal end 345 that includes a suture loading ingress provided as an end slot 346 that leads to a suture slot 347 contained in both the lower jaw body 341 and jaw insert 342. The suture slot 347 proximally terminates at a proximal suture retention node or slot end 348 where the suture resides, as further detailed below, prior to deployment when the suture is picked up by the needle and a loop of the suture is passed through the tissue held between the jaws.

Figure 44:
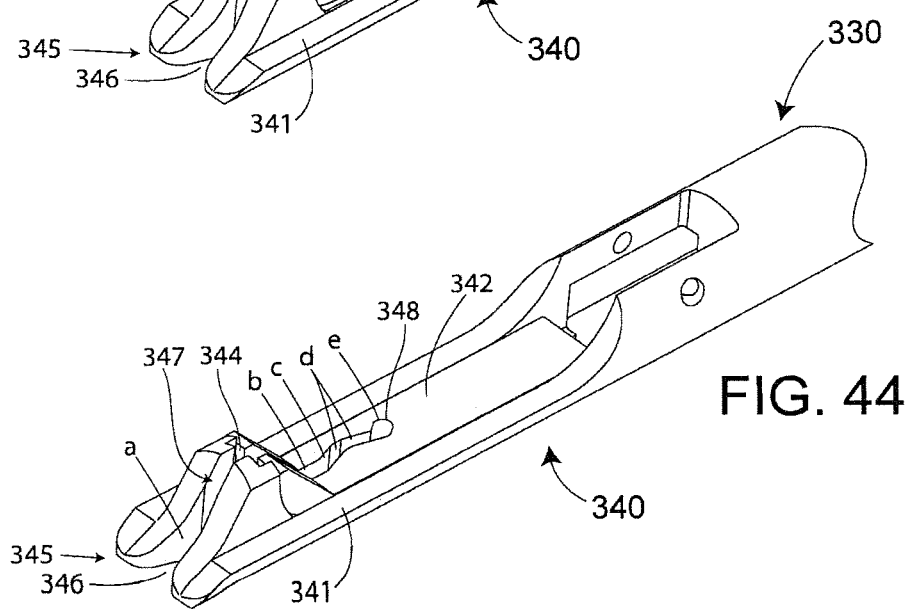
FIG. 44 is an enlarged close-up corresponding to FIG. 43, but as assembled.

In this embodiment, as best shown in FIGS. 44 and 46, the suture slot 37 has varying dimensions along its length in order to provide friction within portions of the slot relative to the suture to be deployed. As such, these dimensions vary relative to the suture to be passed by the device 310. The presently preferred device is intended for use with a range of suture, from #2 suture to #2-0 suture. The thicker #2 suture has a nominal diameter of about 0.5 mm, or about 0.0196", and the thinner #2-0 suture has a nominal diameter of about 0.3 mm, or about 0.0118". All further dimensions will be in inches. While this embodiment can accommodate a particular range of suture sizes, e.g., #2 to #2-0 suture, the dimensions can be adjusted as needed to accommodate any conventional suture size or range of conventional suture sizes.

Although this is an exemplary embodiment and the principals of the underlying invention can be varied to accommodate different size suture, a detailed review of this embodiment's dimensions may be helpful to the reader. At location "a" near the suture loading ingress or end slot 346, the width is much larger than the diameter of the suture so that the suture is easily pulled into the end slot 346 and down into the suture slot 347. At location "b" which extends on either side of the vertical portion of needle channel 343, the width is 0.024±001 such that the #2 suture may continue to pass freely through this portion of the suture channel 347. At location "c," the width of the suture channel 347 narrows to 0.020±001 such that the channel begins to closely conform to the suture's nominal diameter. At locations labeled "d," the suture channel 347 narrows further to 0.019±001 such that there is a friction fit between the channel 347 and the suture. And finally, when the suture is pulled allows to the end of the suture channel 347 and into its proximal suture retention node 348, the width expands to 0.026±001, thereby allowing the surgeon to make vertical adjustments to the suture as desired prior to deployment to the surgical site.

Generally, the surgeon will leave a relatively short tag of suture extending below the underside of the lower jaw 340 such that, after the device passes a loop of suture through the tissue, only that amount of suture need be pulled through the tissue by subsequently pulling on the loop before a single strand of suture remains. Moreover, after the device 310 is retracted from the surgical site, it is immediately ready to be reloaded with suture because the needle spring 386, shown in FIG. 41 and described above, automatically retracts the needle to the non-deployed or resting state and biases it in that position, whereby a new suture can be loaded.

FIGS. 49a and b to 56a and b are a succession of paired figures that illustrate some structural nuances and overall operation of the preferred embodiment. In particular, these figures show the overall operation—all the way from the loading of the suture through the suture loading ingress or end slot, the forward translation and momentary sideways movement of the needle as it engages the suture, the creation of a suture loop passed through the target tissue (the tissue has been omitted for clarity), and the retraction of the needle to the resting position.

FIGS. 49a and b show the position of the needle 400 relative to the suture slot 347 and proximal suture retention node 348 when the needle 400 is in the retracted or resting state.

FIGS. 50a and b show a length of suture 34 being initially pulled through the end slot 346 and down into the suture slot 347. Normally, the moveable jaw 350 would be closed prior to the loading of the suture 34, or at least prior to introduction of the device 310 to the surgical site, but here the moveable jaw 350 is consistently shown in the open position in order to simplify the view.

FIGS. 51a and b show the suture 34 pulled a bit deeper into the suture slot 347. At this junction, in this particular embodiment, the suture 34 is being pulled into that part of the suture slot 347 that takes a non-linear path and that begins to narrow (see FIGS. 44 and 46 and related description). This geometry, or equivalent, provides sufficient friction to keep the suture in the suture slot 347 during deployment.

FIGS. 52a and b show the suture 34 at the point where it has been fully loaded into the proximal suture retention node 348 at the end of the suture slot 347. In this embodiment, as can best be seen by looking back and forth between FIGS. 51b and 52b, the non-linear geometry of the suture slot 347 also causes the needle tip 404 to be laterally tucked off to the side of the suture slot 347 so that the suture 34 does not hang up on the tip 404 when being pulled toward the proximal end of the suture slot 347. This arrangement beneficially prevents the suture 34 from being nicked as it is loaded. Also, as best shown in FIG. 52b, after the suture 34 is safely located proximally to the needle tip 404, the sideward or lateral deflection of the needle provides a subtle spring force that is directed to the right (upward in the figure). This squeezes the suture 34 between the needle's notch-side ramp 406 and the opposite of the proximal suture retention node 348, thereby helping retain the suture in place prior to placement without any further action by the surgeon. The foregoing arrangement constitutes a means for retaining the suture 34 within the suture slot 347 prior to deployment. Other suitable structure may be used to accomplish this retention function, of course, including, but not limited to squeezing or pinching arrangements, friction based arrangements, a close relationship between the diameter of the suture and the dimensions of the suture slot, etc.

Continuing with the remaining FIGS. 53-56, please note that tissue would ordinarily be clamped between the lower jaw 340 and the moveable jaw 350 prior to and during deployment of the needle 400 and placement of the suture 34. In other words, during needle deployment, the moveable jaw 350 would ordinarily be partially closed, as opposed to fully open as shown. However, in order to keep FIGS. 53-56 similar to FIGS. 49-52 and clarify what is shown, the tissue is omitted and the moveable jaw 350 in shown in the fully open position.

FIGS. 53a and b show the position of the needle 400 relative to the lower jaw 340, suture slot 347, and suture 34, as the needle 400 is translated forward to the distal end of the device with the needle trigger 381 (see FIG. 41). As shown in FIG. 53b, the suture channel 343 (see also the side view in FIG. 48) includes a deflection relief 349 that permits the needle 400 to deflect to the left as it slides forward past the suture 34.

FIGS. 54a and b show the position of the various components after the needle 400 has been moved forward to the point that its needle notch 405 is aligned with the proximal suture retention node 348 and an intermediate portion of the suture 34 contained therein. By this point, a notch-side ramp 406 of the needle has cleared the suture 34 such that the needle 400 snaps back in line or springs back to the right and the intermediate portion of the suture 34 is surrounded by or captured in the needle notch 405.

FIGS. 55a and b shows the system after the needle 400 and needle notch 405 has been bent around the curve of the lower jaw's needle channel 343, thereby carrying a loop of the suture 34 out of the needle exit 344 of the lower jaw 340. If tissue were held between the lower and upper jaws 340, 350, then this loop of suture 343 would have been pushed or passed through that tissue.

FIGS. 56a and b, lastly, shows the needle 400 after it has automatically returned to its internal resting state within the needle channel 343 of the lower jaw 340. In this position, i.e. after passing the suture, the overall suture passing device 310 can be simply pulled proximally away from the surgical site, the loop of suture 340 sliding out of the end slot 346 at the distal end of the device 310. The jaws 340, 350 of the suture passing device 310, or a separate set of forceps, can then be used to pull the loop of suture 34 through the tissue. Note that the device 310, if desired by the surgeon, is automatically ready to load another length of suture 34 into the end slot 346 for further suture passing activity.

In all embodiments, it is to be expressly understood that a disposable needle may be employed. It will be appreciated, therefore, that a system or kit is provided wherein the suturing apparatus (excluding the needle) may be re-used while the disposable needles are replaced.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A suturing apparatus, comprising:
   a first jaw defining an ingress;
   a second jaw movable with respect to the first jaw;
   a bendable needle carried by the first jaw and movable between a proximal position and a distal position, the needle defining a needle slot that aligns with the ingress to enable loading of a suture through the ingress into the needle slot; and
   wherein the second jaw further comprises an integral suture receiver, the suture receiver comprising a flap in the second jaw, wherein the flap is removable from the second jaw.

2. A suturing apparatus, comprising:
   a first jaw and a second jaw movable with respect to each other;
   a bendable needle carried by the first jaw and adapted to carry a suture, the needle being movable between a first position wherein the needle is substantially housed within the first jaw and a second position wherein a distal portion of the needle protrudes from the first jaw;
   means for securing the suture in place prior to being carried by the bendable needle; and
   a suture receiver disposed adjacent to the second jaw and configured to disengage the suture carried by the bendable needle, the suture receiver comprising a flap in the second jaw, wherein the flap is removable from the second jaw.

3. The apparatus of claim 2, wherein the suture receiver comprises a flap elastically deformable by the needle as it moves to the second position.

4. The apparatus of claim 3, wherein the flap disengages the suture carried by the bendable needle by returning to its non-deformed state as the needle is moved back to its first position.

5. A suturing apparatus, comprising:
   a first jaw defining an ingress;
   a second jaw movable with respect to the first jaw;
   a bendable needle carried by the first jaw and movable between a proximal position and a distal position, the needle defining a needle slot that aligns with the ingress to enable loading of a suture through the ingress into the needle slot; and
   a suture receiver disposed adjacent to the second jaw, the suture receiver comprising a flap, wherein the flap is removable.

6. The apparatus of claim 5, wherein the flap is elastic.

* * * * *